(12) United States Patent
Zhou et al.

(10) Patent No.: US 9,068,170 B2
(45) Date of Patent: Jun. 30, 2015

(54) GENERATION OF PLURIPOTENT STEM CELLS USING RECOMBINANT PROTEINS

(75) Inventors: Hongyan Zhou, San Diego, CA (US); Sheng Ding, Pasadena, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 319 days.

(21) Appl. No.: 12/723,063

(22) Filed: Mar. 12, 2010

(65) Prior Publication Data

US 2010/0233804 A1 Sep. 16, 2010

Related U.S. Application Data

(63) Continuation-in-part of application No. PCT/US2009/037429, filed on Mar. 17, 2009.

(60) Provisional application No. 61/069,956, filed on Mar. 17, 2008, provisional application No. 61/197,986, filed on Oct. 31, 2008.

(51) Int. Cl.
*C12N 5/074* (2010.01)
*C12N 15/85* (2006.01)

(52) U.S. Cl.
CPC .......... *C12N 5/0696* (2013.01); *C12N 2500/14* (2013.01); *C12N 2501/01* (2013.01); *C12N 2501/065* (2013.01); *C12N 2501/15* (2013.01); *C12N 2510/00* (2013.01); *C12N 15/85* (2013.01); *C12N 2501/602* (2013.01); *C12N 2501/603* (2013.01); *C12N 2501/605* (2013.01); *C12N 2501/608* (2013.01); *C12N 2501/727* (2013.01); *C12N 2506/08* (2013.01)

(58) Field of Classification Search
CPC ............... C12N 15/85; C12N 2501/15; C12N 2501/01; C12N 2500/14; C12N 2501/065; C12N 2510/00; C12N 5/0696; C12N 2501/602; C12N 2506/08; C12N 2501/727; C12N 2501/608; C12N 2501/603; C12N 2501/605
See application file for complete search history.

(56) References Cited

U.S. PATENT DOCUMENTS

| | | | |
|---|---|---|---|
| 5,824,837 A | 10/1998 | Chen et al. | |
| 5,843,780 A | 12/1998 | Thomson | |
| 6,200,806 B1 | 3/2001 | Thomson | |
| 7,029,913 B2 | 4/2006 | Thomson | |
| 7,265,138 B2 | 9/2007 | Doherty et al. | |
| 8,298,825 B1 | 10/2012 | Hochedlinger et al. | |
| 8,603,818 B1 | 12/2013 | Hochedlinger et al. | |
| 8,906,677 B2 | 12/2014 | Li et al. | |
| 2002/0142457 A1 | 10/2002 | Umezawa et al. | |
| 2004/0157324 A1 | 8/2004 | Spradling et al. | |
| 2006/0182724 A1 | 8/2006 | Riordan | |
| 2007/0032447 A1 | 2/2007 | Eilertsen | |
| 2007/0128719 A1 | 6/2007 | Tseng et al. | |
| 2007/0134215 A1 | 6/2007 | Fukuda et al. | |
| 2007/0141703 A1 | 6/2007 | Stanley et al. | |
| 2007/0161107 A1 | 7/2007 | Mummery et al. | |
| 2007/0172946 A1 | 7/2007 | Smith et al. | |
| 2007/0196919 A1 | 8/2007 | Reh et al. | |
| 2007/0254359 A1 | 11/2007 | Rezania et al. | |
| 2007/0259423 A1 | 11/2007 | Odorico et al. | |
| 2007/0264709 A1 | 11/2007 | Smith et al. | |
| 2007/0269412 A1 | 11/2007 | Kopyov | |
| 2007/0281355 A1 | 12/2007 | Dalton et al. | |
| 2008/0066197 A1 | 3/2008 | Ying et al. | |
| 2008/0242594 A1 | 10/2008 | McKay et al. | |
| 2008/0268533 A1 | 10/2008 | Dalton et al. | |
| 2009/0068742 A1 | 3/2009 | Yamanaka | |
| 2009/0117439 A1 | 5/2009 | Fujinami et al. | |
| 2009/0203690 A1 | 8/2009 | Akritopoulou-Zanze et al. | |
| 2009/0227032 A1 | 9/2009 | Yamanaka et al. | |
| 2010/0233804 A1 | 9/2010 | Zhou et al. | |
| 2010/0267141 A1 | 10/2010 | Shi et al. | |
| 2011/0033931 A1* | 2/2011 | Schwartz et al. | ............. 435/377 |
| 2011/0039332 A1 | 2/2011 | Sakurada et al. | |
| 2012/0122212 A1 | 5/2012 | Grskovic et al. | |
| 2012/0129172 A1 | 5/2012 | Okano et al. | |
| 2012/0196360 A1 | 8/2012 | Okita et al. | |
| 2015/0079675 A1 | 3/2015 | Li et al. | |

FOREIGN PATENT DOCUMENTS

| | | |
|---|---|---|
| CN | 101356270 | 1/2009 |
| EP | 1970446 A1 | 9/2008 |
| GB | 2 436 737 | 10/2007 |
| GB | 2 450 603 | 12/2008 |
| JP | 2007/508026 | 4/2007 |
| JP | 2008/307007 | 12/2008 |
| JP | 2010/529851 | 9/2010 |
| WO | WO 2007/016566 A2 | 2/2007 |
| WO | 2007/069666 | 6/2007 |
| WO | 2007/113505 | 10/2007 |
| WO | 2008/015418 A2 | 2/2008 |

(Continued)

OTHER PUBLICATIONS

Hudecz et al. Medicinal Research Reviews, 25(6): 679-736, 2005.*
Collas et al. Reproductive BioMedicine Online: 762-770, 2006.*
Oliveri et al. Regenerative Medicine, 2(5): 795-816, Sep. 2007.*
Sullivan et al. Reproductive BioMed. Online, 16(1): 41-50, Nov. 2008.*
Djuric and Ellis, 202, Stem Cell Research and Therapy, 2010,1:3.*
Huangfu et al, 2008, Nature Biotechnology, 26:1269-75.*
Plath et al. Nature Reviews, 12: 253-265, 2011.*

(Continued)

*Primary Examiner* — Thaian N Ton
(74) *Attorney, Agent, or Firm* — Kilpatrick Townsend & Stockton LLP

(57) ABSTRACT

The present invention provides for methods, compositions, and kits of producing an induced pluripotent stem cell from a mammalian non-pluripotent cell using exogenous transcription factors.

14 Claims, 5 Drawing Sheets
(5 of 5 Drawing Sheet(s) Filed in Color)

(56) References Cited

FOREIGN PATENT DOCUMENTS

| WO | 2008/056173 A2 | 5/2008 |
|---|---|---|
| WO | 2008/088882 A2 | 7/2008 |
| WO | 2008/089351 | 7/2008 |
| WO | WO 2008/105630 A1 | 9/2008 |
| WO | 2009/006422 A1 | 1/2009 |
| WO | WO 2009/032194 A1 | 3/2009 |
| WO | WO 2009/032456 A1 | 3/2009 |
| WO | 2009/057831 | 5/2009 |
| WO | WO 2009/067756 A1 | 6/2009 |
| WO | WO 2009/067757 A1 | 6/2009 |
| WO | WO 2009/073523 A2 | 6/2009 |
| WO | 2009/117439 A1 | 9/2009 |
| WO | 2011/047300 A1 | 4/2011 |

OTHER PUBLICATIONS

Silva et al. PLoS Biology,6(10): 2237-2247, Oct. 2008.*
Kim et al., Cell, 136: 411-419, 2009.*
Kim et al., "Generation of Human Induced Pluripotent Stem Cells by Direct Delivery of Reprogramming Proteins," Cell Stem Cell, Jun. 2009, vol. 4, No. 6, pp. 472-476.
Okita et al., "Generation of Mouse Induced Pluripotent Stem Cells Without Viral Vectors," Science, Nov. 2008, vol. 322, pp. 949-953.
Stadtfeld et al., "Induced Pluripotent Stem Cells Generated Without Viral Integration," Science, Nov. 2008, vol. 322, pp. 945-949.
Takahashi, Kazutoshi et al.; "Induction of Pluripotent Stem Cells from Adult Human Fobroblasts by Defined Factors"; 2007, Akahashi, Kazutoshi et al.; "Induction of Pluripotent Stem Cells from Adult Human Fobroblasts by Defined Factors"; 2007, Cell, vol. 131, pp. 1-12., vol. 131, pp. 1-12.
Zhou, Hongyan et al.; Generation of Induced Pluripotent Stem Cells Using Recombinant Proteins; 2009, Cell Stem Cell, vol. 4, pp. 381-384.
Hochedlinger, et al., "Nuclear reprogramming and pluripotency," Nature, Jun. 2006, vol. 441, pp. 1061-1067.
Kubicek, et al., "Reversal of H3K9me2 by a Small-Molecule Inhibitor for the G9a Histone Methyltransferase," Molecular Cell, Feb. 2007, vol. 25, No. 3, pp. 473-481.
Meissner, et al., "Direct reprogramming of genetically unmodified fibroblasts into pluripotent stem cells," Nature Biotechnology, Oct. 2007, vol. 25, No. 10, pp. 1177-1181.
Plews, et al., "Activation of Pluripotency Genes in Human Fibroblast Cells by a Novel mRNA Based Approach," PLoS ONE, Dec. 2010, vol. 5, No. 12, pp. 1-10.
Shi, et al., "A Combined Chemical and Genetic Approach for the Generation of Induced Pluripotent Stem Cells," Cell Stem Cell, Jun. 2008, vol. 2, No. 6, pp. 525-528.
Tada, et al., "Nuclear reprogramming of somatic cells by in vitro hybridization with ES cells," Current Biology, 2001, vol. 11, pp. 1553-1558.
Takahashi, et al., "Induction of Pluripotent Stem Cells from Mouse Embryonic and Adult Fibroblast Cultures by Defined Factors," Cell, Aug. 2006, vol. 126, No. 4, pp. 663-676.
Tojo, et al., "The ALK-5 inhibitor A-83-01 inhibits Smad signaling and epithelia-to-mesenchymal transition by transforming growth factor-β," Cancer Sci, Nov. 2005, vol. 96, No. 11, pp. 791-800.
Wernig, et al., "In vitro reprogramming of fibroblasts into a pluripotent ES-cell-like state," Nature, Jul. 2007, vol. 448, No. 7151, pp. 318-324.
Yamanaka, "Strategies and New Developments in the Generation of Patient-Specific Pluripotent Stem Cells," Cell Stem Cell, Jul. 2007, vol. 1, pp. 39-49.
Beaujean et al., Dev. Biol., 2000, vol. 221, pp. 337-354.
Debs et al., J. Biol. Chem., 1990, vol. 265, pp. 10189-10192.
Ho et al., Cancer Res., 2001, vol. 61, pp. 474-77.
Huangfu et al., 2008, Nature Biotechnology, 26, pp. 795-797.
Krippl et al., Proc. Natl. Acad. Sci. USA, 1984, vol. 81, pp. 6988-6992.
Mi et al., Mol. Ther., 2001, vol. 4, pp. 339-347.
Pan et al., J. Biol. Chem., 2004, vol. 279, pp. 37013-37020.
Roberts et al., (PD98059 Enhanced Insulin, Cytokine, and Growth Factor Activation of Xanthine Oxidoreductase in Epithelial Cells Involves STAT3 and the Glucocoticoid Receptor, Journal of Cellular Biochemistry 2007, 101: 1567-1587.
Sells et al., BioTechniques, 1995, vol. 19, pp. 72-78.
Shields et al., J. Biol. Chem., 1997, vol. 272, pp. 18504-18507.
Stacey et al., Mol. Cell. Biol., 1987, vol. 7, pp. 523-527.
Wadia et al., Curr. Opin. Biotechnol., 2002, vol. 13, pp. 52-56.
Zhao et al., Cell Death and Differentiation, 2007, vol. 14, pp. 489-499.
Zheng et al., Cancer Res., 2003, vol. 63, pp. 6909-6913.
Aasen et al., Nat Biotechnol 26:1276-1284 (2008).
Brons et al., Nature, 2007, vol. 448, pp. 191-195.
Chambers et al., Nature, 2007, vol. 450, pp. 1230-1234.
Chen et al., Proc Natl Acad Sci USA, 2007, vol. 104, pp. 10482-10487.
Chou et al., Cell, 2008, vol. 135, pp. 449-461.
D'Amour et al., Nat Biotechnol, 2005, vol. 23, pp. 1534-1541.
Demers et al., Cloning Stem Cells, 2007, vol. 9, pp. 512-522.
Dimos et al., Science, 2008, vol. 321, pp. 1218-1221.
Dvorak et al., Stem Cells, 2005, vol. 23, pp. 1200-1211.
Feng et al, "Molecules that Promote or Enhance Reprogramming of Somatic Cells to Induced Pluripotent Stem Cells," Cell Stem Cell, 2009, 4, 301-12.
Guo et al., Development, 2009, vol. 136, pp. 1063-1069.
Han et al., Curr Stem Cell Res Ther, 2008, vol. 3, pp. 66-74.
Hayashi et al., Cell Stem Cell, 2008, vol. 3, pp. 391-401.
Hindie et al., "Structure and allosteric effects of low-molecular-weight activators on the protein kinase PDK1," Nat Chem Biol, Oct. 2009, vol. 5, No. 10, pp. 758-764.
Kanatsu-Shinohara et al., Cell, 2004, vol. 119, pp. 1001-1012.
Li et al., "Generation of rat and human induced pluripotent stem cells by combining genetic reprogramming and chemical inhibitors," Cell Stem Cell, 2009, vol. 4, pp. 16-19.
Li et al., Differentiation, 2007, vol. 75, pp. 299-307.
Li et al., "Small molecules that modulate embryonic stem cell fate and somatic cell reprogramming," Trends Pharmacol Sci, Jan. 2010, vol. 31, No. 1, pp. 36-45.
Li et al., Stem Cells 27:2992-3000 (2009).
Lin et al., Nat Methods 6:805-808 (2009).
Lowry et al., Proc Natl Acad Sci USA, 2008, vol. 105, pp. 2883-2888.
Maherali et al., "Directly Reprogrammed Fibroblasts Show Global Epigenetic Remodeling and Widespread Tissue Contribution," Cell Stem Cell, 2007, 1, pp. 55-70.
Maherali et al., "Tgfβ Signal Inhibition Cooperates in the Induction of iPSCs and Replaces Sox2 and cMyc," Current Biology, 2009, vol. 19, pp. 1718-1723.
Muller et al., "Upping the Ante: Recent Advances in Direct Reprogramming," Mol. Ther., 2009, vol. 17, pp. 947-53.
Nakagawa et al., Nat Biotechnol, 2008, vol. 26, pp. 101-106.
Peerani et al., EMBO J., 2007, vol. 26, pp. 4744-4755.
Ruhnke et al., Stem Cells, 2003, vol. 21, pp. 428-436.
Saha et al., Biophys. J., 2008, vol..94, pp. 4123-4133.
Sato et al., Dev. Biol., 2003, vol. 260, pp. 404-413.
Schugar et al., Gene Ther, 2008, vol. 15, pp. 126-135.
Schulze et al., Methods Mol Biol, 2006, vol. 329, pp. 45-58.
Singh et al., Stem Cells, 2007, vol. 25, pp. 2534-2542.
Sylvester et al. (Arch Surg. 136:93-99, 2004).
Taranger et al., "Induction of Dedifferentiation, Genomewide Transcriptional Programming, and Epigenetic Reprogramming by Extracts of Carcinoma and Embryonic Stem Cells," Molecular Biology of the Cell, 2005, vol. 16, pp. 5719-5735.
Tesar et al., Nature, 2007, vol. 448, pp. 196-199.
Toyooka et al., Development, 2008, vol. 135, pp. 909-918.
Ueda et al., PLoS One 3, 2008, e2800.
Wering et al., "c-Myc is Dispensable for Direct Reprogramming of Mouse Fibroblasts," Cell Stem Cell, 2008, 2, 10-12.
Xu et al., Nat. Biotechnol, 2002, vol. 20, pp. 1261-1264.
Xu et al., Nature 453, 338-44 (2008).
Ying et al, Nature, 2008, vol. 453, pp. 519-523.
Ying et al., Cell, 2003, vol. 115, pp. 281-292.
Yu et al., Science, 2007, vol. 318, pp. 1917-1920.

(56) References Cited

OTHER PUBLICATIONS

Zhu et al., "Reprogramming of human primary somatic cells by OCT4 and chemical compounds," Cell Stem Cell, Dec. 3, 2010, vol. 7, No. 6, pp. 651-655.
Office Action mailed Dec. 27, 2011, U.S. Appl. No. 12/759,386.
Office Action mailed Nov. 23, 2012, U.S. Appl. No. 12/933,391.
Artyomov et al., PLoS Comput Biol 6, e1000785 (2010).
Brambrink et al., Cell Stem Cell 2, 151-9 (2008).
Christen et al., BMC Biol 8, 5 (2010).
Claassen et al., "Rock inhibition enhances the recovery and growth of cryopreserved human embryonic stem cells and human induced pluripotent stem cells," Molecular Reproduction and Developments, 2009, vol. 76, No. 8, pp. 722-732.
Ernst et al., "gp130-mediated Signal Transduction in Embryonic Stem Cells Involves Activation of Jak and Ras/Mitogen-activated Protein Kinase Pathways," J. Biol. Chem., Nov. 22, 1996, vol. 271, No. 47, pp. 30163-30143.
Feldman et al., "G9a-mediated irreversible epigenetic inactivation of Oct-3/4 during early embryogenesis," Nature Cell Biology, 2006, vol. 8(2), pp. 188-194.
Graf et al., Nature 462(7273):587-594 (2009).
Han et al., Nat Cell Biol 13(1):66-71 (2011).
Hanna et al., Cell 133, 250-64.
Hanna et al., Nature 462, 595-601 (2009).
Hanna et al, "Treatment of Sickle Cell Anemia Mouse Model with iPS Cells Generated from Autologous Skin," Science, Dec. 21, 2007, vol. 318, pp. 1920-2.
Hochedlinger et al., Development 136, 509-23 (2009).
Ieda et al., Cell 142, 375-86 (2010).
Jia et al., Nat Methods 7(3):197-199 (2010).
Kim et al., "Direct reprogramming of mouse fibroblasts to neural progenitors," Proc. Natl. Acad. Sci., USA, May 10, 2011, vol. 108, No. 9, pp. 7838-7843.
Kuzmenkin et al., Faseb J. 23, 4168-80 (2009).
Mikkelsen et al., Nature 454(7200):49-55 (2008).
Okada et al., Biochem Biophys Acta 1800, 956-63 (2010).
Okita et al., Nature 448, 313-317 (2007).
Schenke-Layland et al., Stem Cell 26, 1537-46 (2008).
Shi "Induction of Pluripotent Stem Cells from Mouse Embryonic Fibroblasts by Oct4 and Klf4 with Small-Molecule Compounds," Cell Stem Cell, 2008, vol. 3, pp. 568-574.
Silva et al., Cell 138, 722-37 (2009).
Sridharan et al., Cell 136(2):364-377 (2009).
Stadtfeld et al., Cell Stem Cell 2, 230-40 (2008).
Stadtfeld et al., Nat Methods 7, 53-55 (2010).
Szabo et al., Nature 468(7323):521-526 (2010).
Takahashi et al., Nat Protoc 2, 3081-9 (2007).
Tighe et al., BMC 8:34 doi//:www.biomedcentral.com/1471-2121/8/34, printout pp. 1-17.
Vierbuchen et al., "Direct conversion of fibroblasts to functional neurons by defined factors," Nature, Feb. 25 2010, vol. 463, No. 7284, pp. 1035-1042.
Warren et al., Cell Stem Cell 7(5):618-630 (2010).
Wernig et al., Nat Biotechnol 26, 916-24 (2008).
Wu et al., "Cellular senescence is an important mechanism of tumor regression upon c-Myc inactivation," Pnas, 2007, vol. 104(32), pp. 13028-13033.
Yamanaka, S. Cell 126, 663-676 (2006).
Zhou et al., Nature 455(7213):627-632 (2008).
Chen et al., "Self-renewal of embryonic stem cells by a small molecule," PNAS, 103(46):17266-17271, 2006.
Watanabe et al., "A ROCK inhibitor permits survival of dissociated human embryonic stem cells," Nature Biotechnology, 25(6):681-868, 2007.
Noggle et al., "A Molecular Basis for Human Embryonic Stem Cell Pluripotency," Stem Cell Reviews and Reports, Jan. 2005, vol. 1(2), pp. 1550-8943; DOI: 10.1385/scr:1:2:111.
Vallier et al., "Activin/Nodal and FGF pathways cooperate to maintain pluripotency of human embryonic stem cells," Journal of Cell Science, Oct. 2005, vol. 118(19), pp. 4495-4509, DOI: 10.1111/J.1432-0436.2006.00143.X.
Wenlin et al., "Generation of novel rat and human pluripotent stem cells by reprogramming and chemical approaches," Methods in Molecular Biology, Jan. 2010, vol. 636, pp. 293-300.
Xiong et al., "Histone deacetylase inhibitors DNA methyltransferase-3B messenger RNA stability and down-regulate de novo Dna methyltransferase activity in human endometrial cells," Cancer Res., Apr. 2005, vol. 65(7), pp. 2684-2689.
Zhou et al., "Conversion of Mouse Epiblast Stem Cells to an Earlier Pluripotency State by Small Molecules," Journal of Biological Chemistry, Sep. 2010, vol. 285(39), pp. 29676-29680; DOI: 10.1074/jbc.C110.150599.
Aoi et al., "Generation of Pluripotent Stem Cells from Adult Mouse Liver and Stomach Cells," Sciencexpress, Feb. 2008, DOI 10.1126/science.1154884, 8 pages.
Lin et al., Nat Methods 6:805-808 (2009), Supplemental Information, 7 pages.
Stadtfeld et al., "Reprogramming of Pancreatic β Cells into Pluripotent Stem Cells," Curr. Biol., Jun. 2008, vol. 18(12): 890, doi: 10.1016/j.cub.2008.05.010.
Hakelien et al., "Transient alteration of cell fate using a nuclear and cytoplasmic extract of an insulinoma cell line," BBRC, vol. 316, pp. 834-841.
Xu et al., "Revealing a core signaling regulatory mechanism for pluripotent stem cell survival and self-renewal by small molecules," PNAS, 2010, vol. 107(8), pp. 8129-8134.

* cited by examiner

```
                        SEQUENCE LISTING

<160> NUMBER OF SEQ ID NOS: 48

<210> SEQ ID NO 1
<211> LENGTH: 11
<212> TYPE: PRT
<213> ORGANISM: Artificial Sequence
<220> FEATURE:
<223> OTHER INFORMATION: synthetic poly-arginine tag, 11 contiguous
      arginines

<400> SEQUENCE: 1

Arg Arg Arg Arg Arg Arg Arg Arg Arg Arg Arg
1               5                   10

<210> SEQ ID NO 2
<211> LENGTH: 20
<212> TYPE: PRT
<213> ORGANISM: Artificial Sequence
<220> FEATURE:
<223> OTHER INFORMATION: synthetic polypeptide enhancing transport
      across membranes, poly-arginine tag plus linker sequence

<400> SEQUENCE: 2

Glu Ser Gly Gly Gly Gly Ser Pro Gly Arg Arg Arg Arg Arg Arg Arg
1               5                   10                  15

Arg Arg Arg Arg
            20

<210> SEQ ID NO 3
<211> LENGTH: 61
<212> TYPE: PRT
<213> ORGANISM: Artificial Sequence
<220> FEATURE:
<223> OTHER INFORMATION: synthetic herpes simplex virus structural
      protein VP22 polypeptide enhancing transport across
      membranes

<400> SEQUENCE: 3

Gly Ser Pro Pro Thr Ala Pro Thr Arg Ser Lys Thr Pro Ala Gln Gly
1               5                   10                  15

Leu Ala Arg Lys Leu His Phe Ser Thr Ala Pro Pro Asn Pro Asp Ala
            20                  25                  30

Pro Trp Thr Pro Arg Val Ala Gly Phe Asn Lys Arg Val Phe Arg Phe
        35                  40                  45
```

```
Ser Pro Gln Thr Ala Arg Arg Ala Thr Thr Thr Arg Ile
    50                  55                  60

<210> SEQ ID NO 4
<211> LENGTH: 26
<212> TYPE: PRT
<213> ORGANISM: Artificial Sequence
<220> FEATURE:
<223> OTHER INFORMATION: synthetic Kaposi FGF signal sequence (kFGF)
      polypeptide enhancing transport across membranes

<400> SEQUENCE: 4

Ala Gly Ser Gly Gly Ala Ala Val Ala Leu Leu Pro Ala Val Leu Leu
1               5                   10                  15

Ala Leu Leu Ala Pro Gly Gly Glu Phe Ala
            20                  25

<210> SEQ ID NO 5
<211> LENGTH: 21
<212> TYPE: PRT
<213> ORGANISM: Artificial Sequence
<220> FEATURE:
<223> OTHER INFORMATION: synthetic protein transduction domain-4 (PTD4)
      polypeptide enhancing transport across membranes

<400> SEQUENCE: 5

Ala Gly Ser Gly Gly Tyr Ala Arg Ala Ala Arg Gln Ala Arg Ala
1               5                   10                  15

Gly Gly Glu Phe Ala
            20

<210> SEQ ID NO 6
<211> LENGTH: 16
<212> TYPE: PRT
<213> ORGANISM: Artificial Sequence
<220> FEATURE:
<223> OTHER INFORMATION: synthetic PENETRATIN polypeptide enhancing
      transport across membranes

<400> SEQUENCE: 6

Arg Gln Ile Lys Ile Trp Phe Gln Gly Arg Arg Met Lys Trp Lys Lys
1               5                   10                  15

<210> SEQ ID NO 7
<211> LENGTH: 11
<212> TYPE: PRT
<213> ORGANISM: Artificial Sequence
<220> FEATURE:
<223> OTHER INFORMATION: synthetic HIV-1 transcriptional activator TAT
      polypeptide enhancing transport across membranes

<400> SEQUENCE: 7

Tyr Gly Arg Lys Lys Arg Arg Gln Arg Arg Arg
1               5                   10

<210> SEQ ID NO 8
<211> LENGTH: 22
<212> TYPE: PRT
<213> ORGANISM: Artificial Sequence
<220> FEATURE:
<223> OTHER INFORMATION: synthetic M918 polypeptide enhancing transport
      across membranes

<400> SEQUENCE: 8

Met Val Thr Val Leu Phe Arg Arg Leu Arg Ile Arg Arg Ala Cys Gly
1               5                   10                  15
```

-continued

Pro Pro Arg Val Arg Val
        20

<210> SEQ ID NO 9
<211> LENGTH: 21
<212> TYPE: PRT
<213> ORGANISM: Artificial Sequence
<220> FEATURE:
<223> OTHER INFORMATION: synthetic TRASPORTAN-10 polypeptide enhancing
      transport across membranes

<400> SEQUENCE: 9

Ala Gly Tyr Leu Leu Gly Lys Ile Gly Leu Lys Ala Leu Ala Ala Leu
 1               5                  10                  15

Ala Lys Lys Ile Leu
        20

<210> SEQ ID NO 10
<211> LENGTH: 11
<212> TYPE: PRT
<213> ORGANISM: Artificial Sequence
<220> FEATURE:
<223> OTHER INFORMATION: synthetic GSK3beta Inhibitor XIII (L803)
<220> FEATURE:
<221> NAME/KEY: MOD_RES
<222> LOCATION: (10)...(10)
<223> OTHER INFORMATION: phosphoserine
<220> FEATURE:
<221> NAME/KEY: MOD_RES
<222> LOCATION: (11)...(11)
<223> OTHER INFORMATION: prolinamide

<400> SEQUENCE: 10

Lys Glu Ala Pro Pro Ala Pro Pro Gln Ser Pro
 1               5                  10

<210> SEQ ID NO 11
<211> LENGTH: 24
<212> TYPE: DNA
<213> ORGANISM: Artificial Sequence
<220> FEATURE:
<223> OTHER INFORMATION: synthetic RT-PCR forward primer for AFP gene

<400> SEQUENCE: 11
acaggaggct atgcatcacc agtt                                            24

<210> SEQ ID NO 12
<211> LENGTH: 24
<212> TYPE: DNA
<213> ORGANISM: Artificial Sequence
<220> FEATURE:
<223> OTHER INFORMATION: synthetic RT-PCR reverse primer for AFP gene

<400> SEQUENCE: 12
tgctcctctg tcagttcagg cttt                                            24

<210> SEQ ID NO 13
<211> LENGTH: 20
<212> TYPE: DNA
<213> ORGANISM: Artificial Sequence
<220> FEATURE:
<223> OTHER INFORMATION: synthetic RT-PCR forward primer for Brachyury
      gene

<400> SEQUENCE: 13
atgccaaaga aagaaacgac                                                 20

```
<210> SEQ ID NO 14
<211> LENGTH: 20
<212> TYPE: DNA
<213> ORGANISM: Artificial Sequence
<220> FEATURE:
<223> OTHER INFORMATION: synthetic RT-PCR reverse primer for Brachyury
      gene

<400> SEQUENCE: 14
agaggctgta gaacatgatt                                              20

<210> SEQ ID NO 15
<211> LENGTH: 24
<212> TYPE: DNA
<213> ORGANISM: Artificial Sequence
<220> FEATURE:
<223> OTHER INFORMATION: synthetic RT-PCR forward primer for cMyc
      proto-oncogene transcription factor gene

<400> SEQUENCE: 15
cagaggagga acgagctgaa gcgc                                         24

<210> SEQ ID NO 16
<211> LENGTH: 28
<212> TYPE: DNA
<213> ORGANISM: Artificial Sequence
<220> FEATURE:
<223> OTHER INFORMATION: synthetic RT-PCR reverse primer for cMyc
      proto-oncogene transcription factor gene

<400> SEQUENCE: 16
ttatgcacca gagtttcgaa gctgttcg                                     28

<210> SEQ ID NO 17
<211> LENGTH: 25
<212> TYPE: DNA
<213> ORGANISM: Artificial Sequence
<220> FEATURE:
<223> OTHER INFORMATION: synthetic RT-PCR forward primer for E-cadherin
      (E-cad) gene

<400> SEQUENCE: 17
gcagtcagat ctccctgagt tcgag                                        25

<210> SEQ ID NO 18
<211> LENGTH: 26
<212> TYPE: DNA
<213> ORGANISM: Artificial Sequence
<220> FEATURE:
<223> OTHER INFORMATION: synthetic RT-PCR reverse primer for E-cadherin
      (E-cad) gene

<400> SEQUENCE: 18
ctacatacaa aggtcactct agcaac                                       26

<210> SEQ ID NO 19
<211> LENGTH: 24
<212> TYPE: DNA
<213> ORGANISM: Artificial Sequence
<220> FEATURE:
<223> OTHER INFORMATION: synthetic RT-PCR forward primer for FoxA2 gene

<400> SEQUENCE: 19
aagggaaatg agaggctgag tgga                                         24

<210> SEQ ID NO 20
```

```
<211> LENGTH: 24
<212> TYPE: DNA
<213> ORGANISM: Artificial Sequence
<220> FEATURE:
<223> OTHER INFORMATION: synthetic RT-PCR reverse primer for FoxA2 gene

<400> SEQUENCE: 20
atgacagatc actgtggccc atct                                          24

<210> SEQ ID NO 21
<211> LENGTH: 21
<212> TYPE: DNA
<213> ORGANISM: Artificial Sequence
<220> FEATURE:
<223> OTHER INFORMATION: synthetic RT-PCR forward primer for GAPDH gene

<400> SEQUENCE: 21
gtgttcctac ccccaatgtg t                                             21

<210> SEQ ID NO 22
<211> LENGTH: 24
<212> TYPE: DNA
<213> ORGANISM: Artificial Sequence
<220> FEATURE:
<223> OTHER INFORMATION: synthetic RT-PCR reverse primer for GAPDH gene

<400> SEQUENCE: 22
attgtcatac caggaaatga gctt                                          24

<210> SEQ ID NO 23
<211> LENGTH: 30
<212> TYPE: DNA
<213> ORGANISM: Artificial Sequence
<220> FEATURE:
<223> OTHER INFORMATION: synthetic RT-PCR forward primer for Kruppel-
      like factor 4 (Klf4) gene

<400> SEQUENCE: 23
caccatggac ccgggcgtgg ctgccagaaa                                    30

<210> SEQ ID NO 24
<211> LENGTH: 27
<212> TYPE: DNA
<213> ORGANISM: Artificial Sequence
<220> FEATURE:
<223> OTHER INFORMATION: synthetic RT-PCR reverse primer for  Kruppel-
      like factor 4 (Klf4) gene

<400> SEQUENCE: 24
ttaggctgtt cttttccggg gccacga                                       27

<210> SEQ ID NO 25
<211> LENGTH: 21
<212> TYPE: DNA
<213> ORGANISM: Artificial Sequence
<220> FEATURE:
<223> OTHER INFORMATION: synthetic RT-PCR forward primer for Nanog gene

<400> SEQUENCE: 25
agggtctgct actgagatgc t                                             21

<210> SEQ ID NO 26
<211> LENGTH: 24
<212> TYPE: DNA
<213> ORGANISM: Artificial Sequence
<220> FEATURE:
<223> OTHER INFORMATION: synthetic RT-PCR reverse primer for Nanog gene
```

<210> SEQ ID NO 27
<211> LENGTH: 24
<212> TYPE: DNA
<213> ORGANISM: Artificial Sequence
<220> FEATURE:
<223> OTHER INFORMATION: synthetic RT-PCR forward primer for
      octamer-binding protein 4 (Oct4, Oct3/4, Pou5f1)
      gene

<400> SEQUENCE: 27
ctgagggcca ggcaggagca cgag                                         24

<210> SEQ ID NO 28
<211> LENGTH: 24
<212> TYPE: DNA
<213> ORGANISM: Artificial Sequence
<220> FEATURE:
<223> OTHER INFORMATION: synthetic RT-PCR reverse primer for
      octamer-binding protein 4 (Oct4, Oct3/4, Pou5f1)
      gene

<400> SEQUENCE: 28
ctgtagggag ggcttcgggc actt                                         24

<210> SEQ ID NO 29
<211> LENGTH: 22
<212> TYPE: DNA
<213> ORGANISM: Artificial Sequence
<220> FEATURE:
<223> OTHER INFORMATION: synthetic RT-PCR forward primer for Otx2 gene

<400> SEQUENCE: 29
ccgactttgc gcctccaaac aa                                           22

<210> SEQ ID NO 30
<211> LENGTH: 22
<212> TYPE: DNA
<213> ORGANISM: Artificial Sequence
<220> FEATURE:
<223> OTHER INFORMATION: synthetic RT-PCR reverse primer for Otx2 gene

<400> SEQUENCE: 30
ggttgatgga cccttctaag gc                                           22

<210> SEQ ID NO 31
<211> LENGTH: 24
<212> TYPE: DNA
<213> ORGANISM: Artificial Sequence
<220> FEATURE:
<223> OTHER INFORMATION: synthetic RT-PCR forward primer for Pax6 gene

<400> SEQUENCE: 31
gcttcatccg agtcttcccg ttag                                         24

<210> SEQ ID NO 32
<211> LENGTH: 21
<212> TYPE: DNA
<213> ORGANISM: Artificial Sequence
<220> FEATURE:
<223> OTHER INFORMATION: synthetic RT-PCR reverse primer for Pax6 gene

<400> SEQUENCE: 32
ccatcttgct tgggaaatcc g                                          21

<210> SEQ ID NO 33
<211> LENGTH: 22
<212> TYPE: DNA
<213> ORGANISM: Artificial Sequence
<220> FEATURE:
<223> OTHER INFORMATION: synthetic RT-PCR forward primer for Pdx1 gene

<400> SEQUENCE: 33
ctccgccgcc accccagttt ac                                         22

<210> SEQ ID NO 34
<211> LENGTH: 22
<212> TYPE: DNA
<213> ORGANISM: Artificial Sequence
<220> FEATURE:
<223> OTHER INFORMATION: synthetic RT-PCR reverse primer for Pdx1 gene

<400> SEQUENCE: 34
gcggggccgg gagatgtatt tg                                         22

<210> SEQ ID NO 35
<211> LENGTH: 22
<212> TYPE: DNA
<213> ORGANISM: Artificial Sequence
<220> FEATURE:
<223> OTHER INFORMATION: synthetic RT-PCR forward primer for Rex-1 gene

<400> SEQUENCE: 35
tgaaagtgag attagccccg ag                                         22

<210> SEQ ID NO 36
<211> LENGTH: 22
<212> TYPE: DNA
<213> ORGANISM: Artificial Sequence
<220> FEATURE:
<223> OTHER INFORMATION: synthetic RT-PCR reverse primer for Rex-1 gene

<400> SEQUENCE: 36
gtcccatccc cttcaatagc ac                                         22

<210> SEQ ID NO 37
<211> LENGTH: 20
<212> TYPE: DNA
<213> ORGANISM: Artificial Sequence
<220> FEATURE:
<223> OTHER INFORMATION: synthetic RT-PCR forward primer for SRY-related
      HMG-box 1 (Sox1) transcription factor gene

<400> SEQUENCE: 37
cctcggatct ctggtcaagt                                            20

<210> SEQ ID NO 38
<211> LENGTH: 20
<212> TYPE: DNA
<213> ORGANISM: Artificial Sequence
<220> FEATURE:
<223> OTHER INFORMATION: synthetic RT-PCR reverse primer for SRY-related
      HMG-box 1 (Sox1) transcription factor gene

<400> SEQUENCE: 38
tacagagccg gcagtcatac                                            20

<210> SEQ ID NO 39
<211> LENGTH: 24

```
<212> TYPE: DNA
<213> ORGANISM: Artificial Sequence
<220> FEATURE:
<223> OTHER INFORMATION: synthetic RT-PCR forward primer for SRY-related
      HMG-box 2 (Sox2) transcription factor gene

<400> SEQUENCE: 39
ggttacctct tcctcccact ccag                                          24

<210> SEQ ID NO 40
<211> LENGTH: 21
<212> TYPE: DNA
<213> ORGANISM: Artificial Sequence
<220> FEATURE:
<223> OTHER INFORMATION: synthetic RT-PCR reverse primer for SRY-related
      HMG-box 2 (Sox2) transcription factor gene

<400> SEQUENCE: 40
tcacatgtgc gacaggggca g                                             21

<210> SEQ ID NO 41
<211> LENGTH: 24
<212> TYPE: DNA
<213> ORGANISM: Artificial Sequence
<220> FEATURE:
<223> OTHER INFORMATION: synthetic RT-PCR forward primer for SRY-related
      HMG-box 17 (Sox17) transcription factor gene

<400> SEQUENCE: 41 tgcccttgt gtataagccc gaga                                           24

<210> SEQ ID NO 42
<211> LENGTH: 24
<212> TYPE: DNA
<213> ORGANISM: Artificial Sequence
<220> FEATURE:
<223> OTHER INFORMATION: synthetic RT-PCR reverse primer for SRY-related
      HMG-box 17 (Sox17) transcription factor gene

<400> SEQUENCE: 42
gggtagttgc aatagtagac cgct                                          24

<210> SEQ ID NO 43
<211> LENGTH: 25
<212> TYPE: DNA
<213> ORGANISM: Artificial Sequence
<220> FEATURE:
<223> OTHER INFORMATION: synthetic bisulfite-sequencing PCR forward
      primer for octamer-binding protein 4 (Oct4, Oct3/4,
      Pou5f1) gene

<400> SEQUENCE: 43
gttgttttgt tttggttttg gatat                                         25

<210> SEQ ID NO 44
<211> LENGTH: 25
<212> TYPE: DNA
<213> ORGANISM: Artificial Sequence
<220> FEATURE:
<223> OTHER INFORMATION: synthetic bisulfite-sequencing PCR reverse
      primer for octamer-binding protein 4 (Oct4, Oct3/4,
      Pou5f1) gene

<400> SEQUENCE: 44
ccaccctcta accttaacct ctaac                                         25

<210> SEQ ID NO 45
```

```
<211> LENGTH: 26
<212> TYPE: DNA
<213> ORGANISM: Artificial Sequence
<220> FEATURE:
<223> OTHER INFORMATION: synthetic bisulfite-sequencing PCR forward
      primer for octamer-binding protein 4 (Oct4, Oct3/4,
      Pou5f1) gene

<400> SEQUENCE: 45
atgggttgaa atattgggtt tattta                                          26

<210> SEQ ID NO 46
<211> LENGTH: 24
<212> TYPE: DNA
<213> ORGANISM: Artificial Sequence
<220> FEATURE:
<223> OTHER INFORMATION: synthetic bisulfite-sequencing PCR forward
      primer for Nanog gene

<400> SEQUENCE: 46
gaggatgttt tttaagtttt tttt                                            24

<210> SEQ ID NO 47
<211> LENGTH: 25
<212> TYPE: DNA
<213> ORGANISM: Artificial Sequence
<220> FEATURE:
<223> OTHER INFORMATION: synthetic bisulfite-sequencing PCR reverse
      primer for Nanog gene

<400> SEQUENCE: 47
cccacactca tatcaatata ataac                                           25

<210> SEQ ID NO 48
<211> LENGTH: 25
<212> TYPE: DNA
<213> ORGANISM: Artificial Sequence
<220> FEATURE:
<223> OTHER INFORMATION: synthetic bisulfite-sequencing PCR forward
      primer for Nanog gene

<400> SEQUENCE: 48
aatgtttatg gtggattttg taggt                                           25
```

GENERATION OF PLURIPOTENT STEM CELLS USING RECOMBINANT PROTEINS

CROSS-REFERENCES TO RELATED APPLICATIONS

This application is a continuation-in-part of PCT/US2009/037429 (published as WO2009/117439) filed Mar. 17, 2009 entitled "Combined Chemical and Genetic Approaches for Generation of Induced Pluripotent Stem Cells" which, in turn, claims the benefit of prior-filed provisional patent application U.S. Ser. Nos. 61/069,956, filed Mar. 17, 2008, and 61/197,986, filed Oct. 31, 2008. The entire content of the above-referenced applications is incorporated herein by reference for all purposes.

BACKGROUND OF THE INVENTION

A recent breakthrough of using defined genetic manipulation, i.e. viral transduction of few genes highly and/or specifically expressed in mouse or human embryonic stem (ES) cells, in reprogramming both mouse and human somatic cells to induced pluripotent stem (iPS) cells has opened up tremendous opportunities to generate patient-specific stem cells for various applications (e.g. cell-based therapy or drug discovery) without the controversies associated with the conventional human ES cells, as well as to study the epigenetic reversal process. Ultimate clinical application of an iPS-cell approach would largely require methods of directed differentiation of human iPS cells for generating homogenous populations of lineage-specific cell types as well as eliminating risks associated with the current iPS-cell drawbacks of genetic manipulation and low efficiency/slow kinetics.

To address the safety issues arose from harboring integrated exogenous sequences in the target cell genome, a number of modified genetic methods have been developed and produced iPS cells with potentially reduced risks (for discussion see Yamanaka, S., *Cell*, 137(1) 13-17 (2009)).

BRIEF SUMMARY OF THE INVENTION

The present invention provides for methods of producing an induced pluripotent stem cell from a mammalian non-pluripotent cell. In some embodiment, the method comprising: contacting the non-pluripotent cell with one or more different exogenous polypeptides, the exogenous polypeptides comprising a transcription factor fused to a heterologous peptide sequence that enhances transport across cell membranes, under conditions to produce the induced pluripotent stem cell from the mammalian non-pluripotent cell; wherein the transcription factor is selected from the group consisting of a Klf polypeptide, an Oct polypeptide, a Myc polypeptide, and a Sox polypeptide.

In some embodiments, the heterologous peptide is selected from the group consisting of *Drosophila* homeoprotein antennapedia transcription protein (AntHD), herpes simplex virus structural protein VP22, the HIV-1 transcriptional activator TAT protein, Kaposi FGF signal sequence (kFGF), protein transduction domain-4 (PTD4), Penetratin, M918, Transportan-10, a nuclear localization sequence, a PEP-I peptide; an amphipathic peptide; a delivery enhancing transporter, and a peptide sequence comprising at least 5 or more contiguous arginines.

In some embodiments, the heterologous peptide is a peptide sequence comprising RRRRRRRRRRR (SEQ ID NO:1).

In some embodiments, the non-pluripotent cell is contacted with (a) a first exogenous polypeptide comprising a first transcription factor selected from a Klf polypeptide, an Oct polypeptide, a Myc polypeptide, and a Sox polypeptide; and (b) a second exogenous polypeptide comprising a second transcription factor selected from a Klf polypeptide, an Oct polypeptide, a Myc polypeptide, and a Sox polypeptide, wherein the first and second transcription factors are different.

In some embodiments, the non-pluripotent cell is further contacted with (c) a third exogenous polypeptide comprising a third transcription factor selected from a Klf polypeptide, an Oct polypeptide, a Myc polypeptide, and a Sox polypeptide, wherein the third transcription factor is different from the first and the second transcription factor.

In some embodiments, the first transcription factor is a Klf polypeptide, the second transcription factor is an Oct polypeptide, and the third transcription factor is a Sox polypeptide.

In some embodiment, the non-pluripotent cell is further contacted with (d) a fourth exogenous polypeptide comprising a fourth transcription factor selected from a Klf polypeptide, an Oct polypeptide, a Myc polypeptide, and a Sox polypeptide, wherein the fourth transcription factor is different from the first and the second and the third transcription factor.

In some embodiments, the non-pluripotent cell is not contacted with a Nanog polypeptide.

In some embodiments, the non-pluripotent cell is not contacted with a protein delivery agent.

In some embodiments, the contacting step comprises at least two cycles of:
i. contacting the non-pluripotent cell with the one or more exogenous polypeptides followed by culturing the cell in the absence of the exogenous polypeptides. In some embodiments, the method further comprises purifying the pluripotent cell to generate a homogenous population of the pluripotent cell In some embodiments, the cell is a mouse cell. In some embodiment, the cell is a human cell. In some embodiment, the cell is a non-human cell.

In some embodiments, the method further comprises contacting the cell with one or more of: a MEK inhibitor; a GSK3 inhibitor; a TGFβ receptor inhibitor or an ALK5 inhibitor; an histone deacetylase (HDAC) inhibitor; and a DNA methyltransferase (DNMT) inhibitor.

In some embodiments, the method further comprises contacting the cell with one or more of: an agent that inhibits H3K9 methylation; an L-type Ca channel agonist; an activator of the cAMP pathway; a nuclear receptor ligand; an erk inhibitor, a MEK inhibitor; a GSK3 inhibitor; a TGFβ receptor inhibitor or an ALK5 inhibitor; an histone deacetylase (HDAC) inhibitor; and a DNA methyltransferase (DNMT) inhibitor.

The present invention also provides for an isolated polypeptide comprising a transcription factor fused to a heterologous peptide sequence that enhances transport across cell membranes. In some embodiments, the transcription factor is selected from the group consisting of: an Oct polypeptide, a Klf polypeptide, a Myc polypeptide, and a Sox polypeptide.

In some embodiments, the heterologous peptide is selected from the group consisting of *Drosophila* homeoprotein antennapedia transcription protein (AntHD), herpes simplex virus structural protein VP22, the HIV-1 transcriptional activator TAT protein, Kaposi FGF signal sequence (kFGF), protein transduction domain-4 (PTD4), Penetratin, M918, Transportan-10, a nuclear localization sequence, a PEP-I peptide; an amphipathic peptide; a delivery enhancing transporter, and a peptide sequence comprising at least 5 or more contiguous arginines.

In some embodiments, the heterologous peptide is a peptide sequence comprising RRRRRRRRRRR (SEQ ID NO:1).

In some embodiments, the transcription factor is a human or mouse polypeptide.

The present invention also provides for an isolated nucleic acid encoding the polypeptide described above.

The present invention also provides for a vector comprising the nucleic acid as described above.

The present invention also provides for a cell comprising the vector as described above.

The present invention also provides for a mixture comprising at least one polypeptide as described above; and a non-pluripotent mammalian cell.

In some embodiments, the mixture comprises:
(a) a first exogenous polypeptide of claim 16 comprising a first transcription factor selected from a Klf polypeptide, an Oct polypeptide, a Myc polypeptide, and a Sox polypeptide; and
(b) a second exogenous polypeptide of claim 16 comprising a second transcription factor selected from a Klf polypeptide, an Oct polypeptide, a Myc polypeptide, and a Sox polypeptide.

In some embodiments, the mixture further comprises:
(c) a third exogenous polypeptide of claim 16 comprising a third transcription factor selected from a Klf polypeptide, an Oct polypeptide, a Myc polypeptide, and a Sox polypeptide.

In some embodiments, the first transcription factor is a Klf polypeptide, the second transcription factor is an Oct polypeptide, and the third transcription factor is a Sox polypeptide.

In some embodiments, the mixture further comprises:
(d) a fourth exogenous polypeptide of claim 16 comprising a fourth transcription factor selected from a Klf polypeptide, an Oct polypeptide, a Myc polypeptide, and a Sox polypeptide.

In some embodiments, the mixture does not comprises an Nanog polypeptide.

In some embodiments, the mixture comprises one or more of: a MEK inhibitor; a GSK3 inhibitor; a TGFβ inhibitor; an histione deacetylase (HDAC) inhibitor; and a DNA methyltransferase (DNMT) inhibitor.

In some embodiments, the mixture further comprises one or more of: an agent that inhibits H3K9 methylation; an L-type Ca channel agonist; an activator of the cAMP pathway; a nuclear receptor ligand; an erk inhibitor a MEK inhibitor; a GSK3 inhibitor; a TGFβ receptor inhibitor or an ALK5 inhibitor; an histione deacetylase (HDAC) inhibitor; and a DNA methyltransferase (DNMT) inhibitor.

The present invention also provides at least one polypeptide as described above. In some embodiments, the kit comprises:
(a) a first exogenous polypeptide of claim 16 comprising a first transcription factor selected from a Klf polypeptide, an Oct polypeptide, a Myc polypeptide, and a Sox polypeptide; and
(b) a second exogenous polypeptide of claim 16 comprising a second transcription factor selected from a Klf polypeptide, an Oct polypeptide, a Myc polypeptide, and a Sox polypeptide.

In some embodiments, the kit further comprises:
(c) a third exogenous polypeptide of claim 16 comprising a third transcription factor selected from a Klf polypeptide, an Oct polypeptide, a Myc polypeptide, and a Sox polypeptide.

In some embodiments, the kit further comprises:
(d) a fourth exogenous polypeptide of claim 16 comprising a fourth transcription factor selected from a Klf polypeptide, an Oct polypeptide, a Myc polypeptide, and a Sox polypeptide.

In some embodiments, the kit does not comprise a Nanog polypeptide.

In some embodiments, the kit further comprises one or more of: a MEK inhibitor; a GSK3 inhibitor; a TGFβ inhibitor; an histione deacetylase (HDAC) inhibitor; and a DNA methyltransferase (DNMT) inhibitor.

In some embodiments, the kit further comprises one or more of: an agent that inhibits H3K9 methylation; an L-type Ca channel agonist; an activator of the cAMP pathway; a nuclear receptor ligand; an erk inhibitor, a MEK inhibitor; a GSK3 inhibitor; a TGFβ receptor inhibitor or an ALK5 inhibitor; an histione deacetylase (HDAC) inhibitor; and a DNA methyltransferase (DNMT) inhibitor.

Other embodiments of the invention will be clear from a reading of the entire application.

BRIEF DESCRIPTION OF THE DRAWINGS

The patent or patent application file contains at least one drawing executed in color. Copies of this patent or patent application publication with color drawing(s) will be provided by the U.S. Patent and Trademark Office upon request and payment of the necessary fee.

DETAILED DESCRIPTION OF THE INVENTION

Definitions

Figure 1:
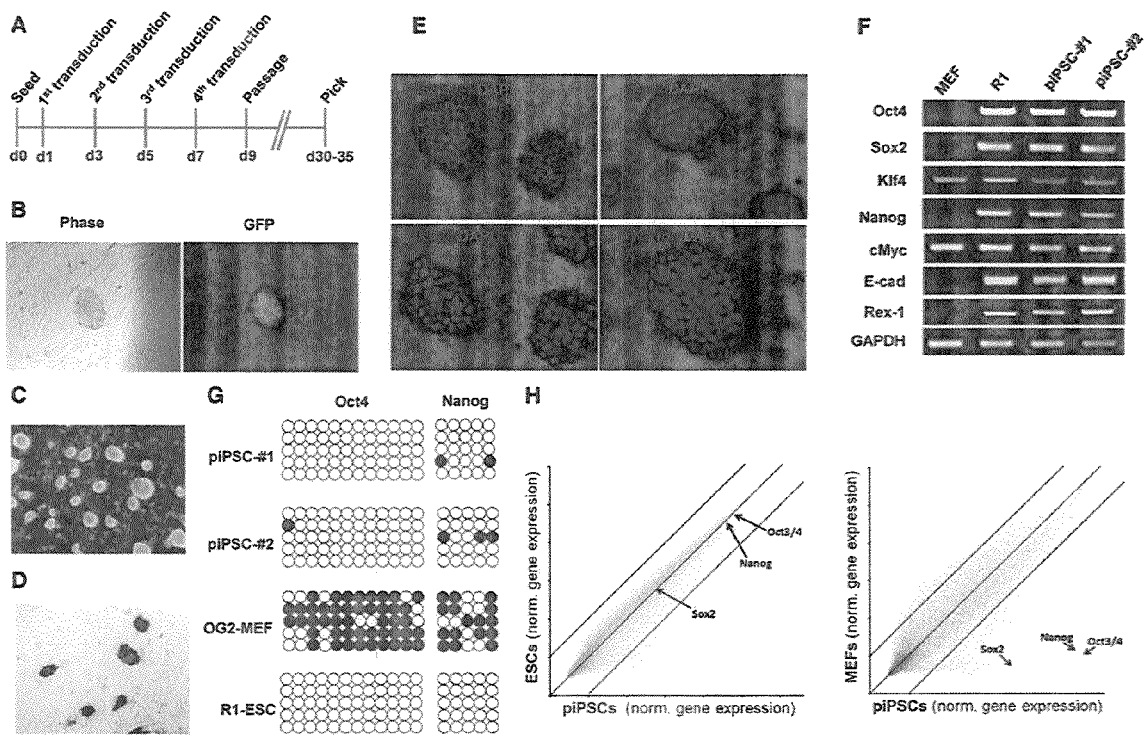
FIG. 1. Generation of protein induced pluripotent stem (piPS) cells by recombinant reprogramming proteins. (A) Timeline of piPS cell generation. (B) Oct4-GFP$^+$ piPS cell colonies were initially observed around day 30-35. Representative phase contrast image (left) and fluorescence image (right) are shown. (C) Oct4-GFP$^+$ piPS cells sustain long term and homogenous self-renewal under conventional mESC growth condition. (D) The long-term expanded piPS cells grow as compact and domed colonies that express strong ALP, a typical pluripotency marker. (E) piPS cells express other typical pluripotency markers, examined by immunofluorescence, including SSEA-1, Sox2, Oct4 and Nanog. DAPI staining was performed to visualize the nuclei, and the images were merged. (F) RT-PCR analysis of endogenous pluripotency gene expression in piPS cells. (G) Methylation analysis of Oct4 and Nanog promoters by bisulfite genomic sequencing. Open and closed circles indicate unmethylated and methylated CpGs, respectively. (H) Scatter plots comparing global gene expression patterns between piPS with murine ES cells, and between piPS cells and OG2-MEFs. The positions of the pluripotency genes Oct4, Nanog, and Sox2 are shown by arrows. Black lines indicate the linear equivalent and twofold changes in gene expression levels between the samples.

A "Nanog polypeptide" refers to any of the naturally-occurring members of Nanog family of transcription factors, or variants thereof that maintain transcription factor activity, similar (within at least 50%, 80%, or 90% activity) compared to the closest related naturally occurring family member, or polypeptides comprising at least the DNA-binding domain of the naturally occurring family member, and optionally comprising a transcriptional activation domain. See, Cavaleri, F. & Schöler, H. R. Cell 11, 643-655 (2003). In some embodiments, variants have at least 90% amino acid sequence identity across their whole sequence compared to a naturally occurring Nanog polypeptide family member such as to those listed above.

An "Oct polypeptide" refers to any of the naturally-occurring members of Octamer family of transcription factors, or variants thereof that maintain transcription factor activity, similar (within at least 50%, 80%, or 90% activity) compared to the closest related naturally occurring family member, or polypeptides comprising at least the DNA-binding domain of the naturally occurring family member, and can further comprise a transcriptional activation domain. Exemplary Oct polypeptides include, Oct-1, Oct-2, Oct-3/4, Oct-6, Oct-7, Oct-8, Oct-9, and Oct-11. e.g. Oct3/4 (referred to herein as "Oct4") contains the POU domain, a 150 amino acid sequence conserved among Pit-1, Oct-1, Oct-2, and uric-86. See, Ryan, A. K. & Rosenfeld, M. G. Genes Dev. 11, 1207-1225 (1997). In some embodiments, variants have at least 85%, 90%, or 95% amino acid sequence identity across their whole sequence compared to a naturally occurring Oct polypeptide family member such as to those listed above or such as listed in Genbank accession number NP_002692.2 (human Oct4) or NP_038661.1 (mouse Oct4). Oct polypeptides (e.g., Oct3/4) can be from human, mouse, rat, bovine, porcine, or other animals. Generally, the same species of protein will be used with the species of cells being manipulated.

A "Klf polypeptide" refers to any of the naturally-occurring members of the family of Krüppel-like factors (Klfs), zinc-finger proteins that contain amino acid sequences similar to those of the Drosophila embryonic pattern regulator Krüppel, or variants of the naturally-occurring members that maintain transcription factor activity similar (within at least 50%, 80%, or 90% activity) compared to the closest related naturally occurring family member, or polypeptides comprising at least the DNA-binding domain of the naturally occurring family member, and can further comprise a transcriptional activation domain. See, Dang, D. T., Pevsner, J. & Yang, V. W. Cell Biol. 32, 1103-1121 (2000). Exemplary Klf family members include, Klf1, Klf2, Klf3, Klf-4, Klf5, Klf6, Klf7, Klf8, Klf9, Klf10, Klf11, Klf12, Klf13, Klf14, Klf15, Klf16, and Klf17. Klf2 and Klf-4 were found to be factors capable of generating iPS cells in mice, and related genes Klf1 and Klf5 did as well, although with reduced efficiency. See, Nakagawa, et al., Nature Biotechnology 26:101-106 (2007). In some embodiments, variants have at least 85%, 90%, or 95% amino acid sequence identity across their whole sequence compared to a naturally occurring Klf polypeptide family member such as to those listed above or such as listed in Genbank accession number CAX16088 (mouse Klf4) or CAX14962 (human Klf4). Klf polypeptides (e.g., Klf1, Klf4, and Klf5) can be from human, mouse, rat, bovine, porcine, or other animals. Generally, the same species of protein will be used with the species of cells being manipulated. To the extent a Klf polypeptide is described herein, it can be replaced with an estrogen-related receptor beta (Essrb) polypeptide. Thus, it is intended that for each Klf polypeptide embodiment described herein, a corresponding embodiment using Essrb in the place of a Klf4 polypeptide is equally described.

A "Myc polypeptide" refers any of the naturally-occurring members of the Myc family (see, e.g., Adhikary, S. & Eilers, M. Nat. Rev. Mol. Cell. Biol. 6:635-645 (2005)), or variants thereof that maintain transcription factor activity similar (within at least 50%, 80%, or 90% activity) compared to the closest related naturally occurring family member, or polypeptides comprising at least the DNA-binding domain of the naturally occurring family member, and can further comprise a transcriptional activation domain. Exemplary Myc polypeptides include, e.g., c-Myc, N-Myc and L-Myc. In some embodiments, variants have at least 85%, 90%, or 95% amino acid sequence identity across their whole sequence compared to a naturally occurring Myc polypeptide family member, such as to those listed above or such as listed in Genbank accession number CAA25015 (human Myc). Myc polypeptides (e.g., c-Myc) can be from human, mouse, rat, bovine, porcine, or other animals. Generally, the same species of protein will be used with the species of cells being manipulated.

A "Sox polypeptide" refers to any of the naturally-occurring members of the SRY-related HMG-box (Sox) transcription factors, characterized by the presence of the high-mobility group (HMG) domain, or variants thereof that maintain transcription factor activity similar (within at least 50%, 80%, or 90% activity) compared to the closest related naturally occurring family member, or polypeptides comprising at least the DNA-binding domain of the naturally occurring family member, and can further comprise a transcriptional activation domain. See, e.g., Dang, D. T., et al., *Int. J. Biochem. Cell Biol.* 32:1103-1121 (2000). Exemplary Sox polypeptides include, e.g., Sox1, Sox-2, Sox3, Sox4, Sox5, Sox6, Sox7, Sox8, Sox9, Sox10, Sox11, Sox12, Sox13, Sox14, Sox15, Sox17, Sox18, Sox-21, and Sox30. Sox1 has been shown to yield iPS cells with a similar efficiency as Sox2, and genes Sox3, Sox15, and Sox18 have also been shown to generate iPS cells, although with somewhat less efficiency than Sox2. See, Nakagawa, et al., *Nature Biotechnology* 26:101-106 (2007). In some embodiments, variants have at least 85%, 90%, or 95% amino acid sequence identity across their whole sequence compared to a naturally occurring Sox polypeptide family member such as to those listed above or such as listed in Genbank accession number CAA83435 (human Sox2). Sox polypeptides (e.g., Sox1, Sox2, Sox3, Sox15, or Sox18) can be from human, mouse, rat, bovine, porcine, or other animals. Generally, the same species of protein will be used with the species of cells being manipulated.

"H3K9" refers to histone H3 lysine 9. H3K9 modifications associated with gene activity include H3K9 acetylation and H3K9 modifications associated with heterochromatin, include H3K9 di-methylation or tri-methylation. See, e.g., Kubicek, et al., *Mol. Cell* 473-481 (2007).

The term "pluripotent" or "pluripotency" refers to cells with the ability to give rise to progeny that can undergo differentiation, under the appropriate conditions, into cell types that collectively demonstrate characteristics associated with cell lineages from all of the three germinal layers (endoderm, mesoderm, and ectoderm). Pluripotent stem cells can contribute to many or all tissues of a prenatal, postnatal or adult animal. A standard art-accepted test, such as the ability to form a teratoma in 8-12 week old SCID mice, can be used to establish the pluripotency of a cell population, however identification of various pluripotent stem cell characteristics can also be used to detect pluripotent cells.

"Pluripotent stem cell characteristics" refer to characteristics of a cell that distinguish pluripotent stem cells from other cells. The ability to give rise to progeny that can undergo differentiation, under the appropriate conditions, into cell types that collectively demonstrate characteristics associated with cell lineages from all of the three germinal layers (endoderm, mesoderm, and ectoderm) is a pluripotent stem cell characteristic. Expression or non-expression of certain combinations of molecular markers are also pluripotent stem cell characteristics. For example, human pluripotent stem cells express at least some, and optionally all, of the markers from the following non-limiting list: SSEA-3, SSEA-4, TRA-1-60, TRA-1-81, TRA-2-49/6E, ALP, Sox2, E-cadherin, UTF-1, Oct4, Rex1, and Nanog. Cell morphologies associated with pluripotent stem cells are also pluripotent stem cell characteristics.

The term "library" is used according to its common usage in the art, to denote a collection of molecules, optionally organized and/or cataloged in such a way that individual members can be identified. Libraries can include, but are not limited to, combinatorial chemical libraries, natural products libraries, and peptide libraries.

A "recombinant" polynucleotide is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acid.

"Expression cassette" refers to a polynucleotide comprising a promoter or other regulatory sequence operably linked to a sequence encoding a protein.

The terms "promoter" and "expression control sequence" are used herein to refer to an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. Promoters include constitutive and inducible promoters. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

A "heterologous sequence" or a "heterologous nucleic acid", as used herein, is one that originates from a source foreign to the particular host cell, or, if from the same source, is modified from its original form. Thus, a heterologous expression cassette in a cell is an expression cassette that is not endogenous to the particular host cell, for example by being linked to nucleotide sequences from an expression vector rather than chromosomal DNA, being linked to a heterologous promoter, being linked to a reporter gene, etc.

The terms "agent" or "test compound" refer to any compound useful in the screening assays described herein. An agent can be, for example, an organic compound (e.g., a small molecule such as a drug), a polypeptide (e.g., a peptide or an antibody), a nucleic acid (e.g., DNA, RNA, double-stranded, single-stranded, an oligonucleotide, antisense RNA, small inhibitory RNA, micro RNA, a ribozyme, etc.), an oligosaccharide, a lipid. Usually, the agents used in the present screening methods have a molecular weight of less than 10,000 daltons, for example, less than 8000, 6000, 4000, 2000 daltons, e.g., between 50-1500, 500-1500, 200-2000, 500-5000 daltons. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., ability to induce pluripotency under certain conditions such as are described herein, creating variants of the lead compound, and evaluating the property and activity of those variant compounds. Often, high throughput screening (HTS) methods are employed for such an analysis.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)).

"Inhibitors," "activators," and "modulators" of expression or of activity are used to refer to inhibitory, activating, or modulating molecules, respectively, identified using in vitro and in vivo assays for expression or activity of a described target protein (or encoding polynucleotide), e.g., ligands, agonists, antagonists, and their homologs and mimetics. The term "modulator" includes inhibitors and activators. Inhibitors are agents that, e.g., inhibit expression or bind to, partially or totally block stimulation or protease inhibitor activity, decrease, prevent, delay activation, inactivate, desensitize, or down regulate the activity of the described target protein, e.g., antagonists. Activators are agents that, e.g., induce or activate the expression of a described target protein or bind to, stimulate, increase, open, activate, facilitate, enhance activation or protease inhibitor activity, sensitize or up regulate the activity of described target protein (or encoding polynucleotide), e.g., agonists. Modulators include naturally occurring and synthetic ligands, antagonists and agonists (e.g., small chemical molecules, antibodies and the like that function as either agonists or antagonists). Such assays for inhibitors and activators include, e.g., applying putative modulator compounds to cells expressing the described target protein and then determining the functional effects on the described target protein activity, as described above. Samples or assays comprising described target protein that are treated with a potential activator, inhibitor, or modulator are compared to control samples without the inhibitor, activator, or modulator to examine the extent of effect. Control samples (untreated with modulators) are assigned a relative activity value of 100%. Inhibition of a described target protein is achieved when the activity value relative to the control is about 80%, optionally 50% or 25, 10%, 5% or 1%. Activation of the described target protein is achieved when the activity value relative to the control is 110%, optionally 150%, optionally 200, 300%, 400%, 500%, or 1000-3000% or more higher.

As defined herein, the term "different exogenous polypeptides" refer to exogenous polypeptides that differ in their primary amino acid sequences.

I. Introduction

As presented in more detail in the Examples, the inventors have found, surprisingly, that it is possible to produce an induced pluripotent stem cell from a mammalian non-pluripotent cell using exogenous transcription factors, e.g., without introducing a polynucleotide encoding the transcription factors into the non-pluripotent cell. Notably, the inventors have determined that such pluripotency can be achieved by contacting the non-pluripotent cell with one or more different exogenous polypeptides comprising one or more transcription factors under conditions to produce the induced pluripotent stem cell from the mammalian non-pluripotent cell. In some embodiments, the exogenous polypeptides comprise a transcription factor fused to a heterologous peptide sequence that enhances transport across cell membranes.

II. Induction of Pluripotent Stem Cells

A. Methods of Producing an Induced Pluripotent Stem Cell

The present invention expressly provides for exogenous introduction of the polypeptide as a protein into the cell. Therefore, in some embodiments, mammalian non-pluripotent cells are induced to pluripotency by exogenously introducing one or more of a Klf polypeptide, an Oct polypeptide, a Myc polypeptide, and/or a Sox polypeptide into the non-pluripotent cells.

According to the present invention, mammalian non-pluripotent cells can be induced to pluripotency by contacting a non-pluripotent cell with one or more different exogenous polypeptides under conditions to produce an induced pluripotent stem cell from the mammalian non-pluripotent cell. The exogenous polypeptides of the present invention comprise a transcription factor. In some embodiments, the exogenous polypeptides comprise a transcription factor fused to a heterologous peptide sequence that enhances transport across cell membranes. Further, an induced pluripotent stem cell can be produced from a mammalian non-pluripotent cell using a combination of approaches, i.e., introducing an expression cassette encoding a Klf polypeptide, an Oct polypeptide, a Myc polypeptide, and/or a Sox polypeptide into the non-pluripotent cells and contacting the non-pluripotent cell with one or more different exogenous polypeptides under conditions to produce the induced pluripotent stem cell from the mammalian non-pluripotent cells.

The non-pluripotent cell can be contacted with one, two, three, four or more transcription factors. For example, the non-pluripotent cell is contacted with a first exogenous polypeptide comprising a first transcription factor selected from a Klf polypeptide, an Oct polypeptide, a Myc polypeptide, and a Sox polypeptide. The non-pluripotent cell can be further contacted with a second, third, and/or fourth or more different exogenous polypeptides, e.g., selected from a Klf polypeptide, an Oct polypeptide, a Myc polypeptide, and a Sox polypeptide. In some embodiments, the non-pluripotent cell is contacted with three exogenous polypeptides, each of which comprises a different transcription factor. For example, in some embodiments, the first transcription factor is a Klf polypeptide, the second transcription factor is an Oct polypeptide, and the third transcription factor is a Sox polypeptide. In some embodiments, the non-pluripotent cell is contacted with three exogenous polypeptides (e.g., a Klf polypeptide, an Oct polypeptide, and a Sox polypeptide) but not other transcription factors (e.g., a Myc polypeptide). In some embodiments, the non-pluripotent cell is contacted with four exogenous polypeptides, each of which comprises a different transcription factor. For example, the first transcription factor is a Klf polypeptide, the second transcription factor is an Oct polypeptide, the third transcription factor is a Sox polypeptide, and the fourth transcription factor is a Myc polypeptide. In some embodiments, no further transcription factors are contacted to the cells.

The non-pluripotent cell can be contacted with an additional transcription factor other than a Klf polypeptide, an Oct polypeptide, a Myc polypeptide, and a Sox polypeptide. In some embodiments, the additional transcription factor(s) do not include a Nanog polypeptide, i.e., mammalian non-pluripotent cells can be induced to pluripotency without contacting the non-pluripotent cells with a Nanog polypeptide.

In some embodiments, cells are identified that endogenously express a Sox polypeptide and/or a Myc polypeptide, and as a second step an Oct polypeptide and/or a Klf polypeptide is exogenously introduced in the cell, thereby inducing conversion of the cell into a pluripotent cell. In some embodiments, cells are identified that endogenously express an Oct polypeptide and/or a Klf polypeptide and/or a Myc polypeptide, and a Sox polypeptide is exogenously introduced in the cell, thereby inducing conversion of the cell into a pluripotent cell.

B. Transcription Factor Proteins

As noted above, the invention provides for delivery of exogenous proteins to cells, thereby generating pluripotent cells. The inventors have shown that a combination of three or four transcription factor proteins can be added to culture media to generate pluripotent cells. However, in view of this result, it is believed that a fewer number of transcription factors selected from Klf polypeptide, an Oct polypeptide, a Myc polypeptide, and a Sox polypeptide can be used to generate pluripotent cells. Further, the one or more transcription factor can be selected from the group consisting of a Klf polypeptide, an Oct polypeptide, a Myc polypeptide, a Sox polypeptide and optionally an additional transcription factor (e.g., a transcription factor other than a Klf, an Oct, a Myc, and a Sox). In some embodiments, the additional transcription factor is a Nanog polypeptide. In some embodiments, the additional transcription factor is not a Nanog polypeptide.

An exogenous polypeptide of the present invention can comprise a transcription factor without a heterologous peptide sequence. Alternatively, the exogenous polypeptide can comprise a transcription factor polypeptide of interest linked to a heterologous peptide that enhances the ability of the transcription factor to enter the cell, e.g., as a fusion protein. The heterologous peptide can be fused to the N-terminus or the C-terminus of the transcription factor.

In some embodiments, the exogenous polypeptide of the present invention comprises two or more heterologous peptide sequences that enhance transport across membranes, i.e., one heterologous peptide can be fused to the exogenous polypeptide at a position N-terminal to the transcription factor, and a second heterologous peptide can be fused to the exogenous polypeptide at a position C-terminal of the exogenous polypeptide. For example, the first peptide can be a peptide sequence comprising 11 contiguous arginines. The second peptide can be a nuclear localization sequence (NLS are recognized by cytosolic nuclear transport receptors, which transport proteins into the cell nucleus through the Nuclear Pore Complex).

The exogenous polypeptide of the present invention can be produced using techniques standard in the art. For example, the polypeptide may be chemically synthesized, recombinantly produced, or isolated from mammalian cells. These polypeptides comprising mammalian transcription factors are heterologous to E. coli or other bacteria. Therefore, when the polypeptides are produced using an E. coli expression system, often they are isolated from inclusion bodies and require solubilization using strong denaturants, and subsequent refolding.

C. Methods That Enhance Protein Transport Across Cell Membranes

Exogenous introduction of a polypeptide into a cell can occur in any number of ways. In some embodiments, one or more proteins can simply be cultured in the presence of target cells under conditions to allow for introduction of the proteins into the cell. For example, an exogenous polypeptide can be introduced into cells by traditional methods such as lipofection, electroporation, calcium phosphate precipitation, particle bombardment and/or microinjection, or can be introduced into cells by a protein delivery agent. For example, the exogenous polypeptide can be introduced into cells by covalently or noncovalently attached lipids, e.g., by a covalently attached myristoyl group. Lipids used for lipofection are optionally excluded from cellular delivery modules in some embodiments. In some embodiments, the transcription factor polypeptides described herein are exogenously introduced as part of a liposome, or lipid cocktail such as commercially available Fugene6 and Lipofectamine. In another alternative, the transcription factor proteins can be microinjected or otherwise directly introduced into the target cell. In some embodiments, the transcription factor polypeptides are delivered into cells using Profect protein delivery reagents, e.g., Profect-P1 and Profect-P2 (Targeting Systems, El Cajon, Calif.), or using Pro-Ject® transfection reagents (Pierce, Rockford Ill., USA). In some embodiments, the transcription factor polypeptides are delivered into cells using a single-wall nano tube (SWNT).

In some embodiments, the exogenous proteins comprise the transcription factor polypeptide of interest linked (e.g., linked as a fusion protein or otherwise covalently or non-covalently linked) to a polypeptide that enhances the ability of the transcription factor to enter the cell (and optionally the cell nucleus). Examples of polypeptide sequences that enhance transport across membranes include, but are not limited to, the *Drosophila* homeoprotein antennapedia transcription protein (AntHD) (Joliot et al., New Biol. 3: 1121-34, 1991; Joliot et al., Proc. Natl. Acad. Sci. USA, 88: 1864-8, 1991; Le Roux et al., Proc. Natl. Acad. Sci. USA, 90: 9120-4, 1993), the herpes simplex virus structural protein VP22 (Elliott and O'Hare, Cell 88: 223-33, 1997); the HIV-1 transcriptional activator TAT protein (Green and Loewenstein, Cell 55: 1179-1188, 1988; Frankel and Pabo, Cell 55: 1 289-1193, 1988); Kaposi FGF signal sequence (kFGF); protein transduction domain-4 (PTD4); Penetratin, M918, Transportan-10; a nuclear localization sequence, a PEP-I peptide; an amphipathic peptide (e.g., an MPG peptide); delivery enhancing transporters such as described in U.S. Pat. No. 6,730,293 (including but not limited to an peptide sequence comprising at least 5-25 or more contiguous arginines or 5-25 or more arginines in a contiguous set of 30, 40, or 50 amino acids; including but not limited to an peptide having sufficient, e.g., at least 5, guanidino or amidino moieties); and commercially available Penetratin™ 1 peptide, and the Diatos Peptide Vectors ("DPVs") of the Vectocell® platform available from Daitos S.A. of Paris, France. See also, WO/2005/084158 and WO/2007/123667 and additional transporters described therein. Not only can these proteins pass through the plasma membrane but the attachment of other proteins, such as the transcription factors described herein, is sufficient to stimulate the cellular uptake of these complexes. A number of polypeptides capable of mediating introduction of associated molecules into a cell have been described previously and can be adapted to the present invention. See, e.g., Langel (2002) Cell Penetrating Peptides CRC Press, Pharmacology and Toxicology Series.

Exemplary polypeptide sequences that enhance transport across membranes include: VP22: G S P P T A P T R S K T P A Q G L A R K L H F S T A P P N P D A P W T P R V A G F N K R V F R F S P Q T A R R A T T T R I (SEQ ID NO:3); kFGF: A G S G G A A V A L L P A V L L A L L A P G G E F A (SEQ ID NO:4); PTD4: A G S G G Y A R A A A R Q A R A G G E F A (SEQ ID NO:5); PENETRATIN: R Q I K I W F Q G R R M K W K K (SEQ ID NO:6); TAT: Y G R K K R R Q R R R (SEQ ID NO:7); M918: M V T V L F R R L R I R R A C G P P R V R V (SEQ ID NO:8); TRANSPORTAN-10: A G Y L L G K I G L K A L A A L A K K I L (SEQ ID NO:9).

In some embodiments, the polypeptide that enhances transport across membranes is a peptide sequence comprising at least 5 or more contiguous or non-contiguous arginines. In some embodiments, the polypeptide that enhances transport across membranes is a peptide sequence comprising at least 7 or more contiguous or non-contiguous arginines. For example, in some embodiments, the polypeptide that enhances transport across membranes is a peptide sequence comprising 11 contiguous arginines, e.g., ESGGGGSPGR-RRRRRRRRRR (SEQ ID NO:2). In some embodiments, the polypeptide that enhances transport across membranes comprises an arginine-rich sequence, e.g., a peptide sequence comprising at least 5 or more arginines (or at least 7 or more arginines), wherein the arginine residues are not all contiguous, but have at least one or more arginine located close to each other, i.e., having no more than 1, 2, or 3 non-arginine amino acids between the arginines. In some embodiments, the polyarginine (e.g., the contiguous or non-contiguous) region is at least 5, 8, 10, 12, 15, 20, or more amino acids long and has at least e.g., 40%, 50%, 60%, 70%, 80%, 90%, or more arginines.

In some embodiments, an exogenous polypeptide of the present invention can comprise two or more transcription factors, e.g., two transcription factors fused together in a single exogenous polypeptide. In particular, the exogenous polypeptide can comprise two or more transcription factors selected from the group consisting of a Klf polypeptide, an Oct polypeptide, a Myc polypeptide, and a Sox polypeptide.

An exogenous polypeptide linked, or not, to a polypeptide that enhances transport across membranes, can be introduced into cells without using a protein delivery agent (e.g., in the absence of a protein delivery agent). For example, an exogenous polypeptide can be introduced into cells in the absence of Profect protein delivery reagents, Pro-Ject® transfection reagents, or a SWNT.

In some embodiments, the cell into which a polypeptide of interest is introduced is a mammalian cell. In some embodiments, the cells is a human or non-human (e.g., primate, rat, mouse, rabbit, bovine, dog, cat, pig, etc.) cell. The cell can be, e.g., in culture or in a tissue, fluid, etc. and/or from (e.g., in vitro or ex vivo) or in an organism (e.g., in vivo).

D. Culturing of Cells

Cells to be induced to pluripotency can be cultured according to any method known in the art. General guidelines can be found in, e.g., Maherali, et al., *Cell Stem Cell* 3:595-605 (2008).

In some embodiments, the cells are cultured in contact with feeder cells. Exemplary feeder cells include, but are not limited to fibroblast cells, e.g., mouse embryonic fibroblast (MEF) cells. Methods of culturing cells on feeder cells is known in the art.

In some embodiments, the cells are cultured in the absence of feeder cells. Cells, for example, can be attached directly to a solid culture surface (e.g., a culture plate), e.g., via a molecular tether. It has been found that culturing cells induced to pluripotency have a much greater efficiency of induction to pluripotency (i.e., a greater portion of cells achieve pluripotency) when the cells are attached directly to the solid culturing surface compared the efficiency of otherwise identically-treated cells that are cultured on feeder cells. Exemplary molecular tethers include, but are not limited to, matrigel, an extracellular matrix (ECM), ECM analogs, laminin, fibronectin, or collagen. Those of skill in the art however will recognize that this is a non-limiting list and that other molecules can be used to attach cells to a solid surface. Methods for initial attachment of the tethers to the solid surface are known in the art.

As used in this "culturing" section, "cells to be induced to pluripotency" are induced by any method in the art, including, but not limited to the methods described in this application.

As discussed in the Examples, the inventors have found that incubation of cells with the transcription factor polypeptides of the invention for extended periods is toxic to the cells. Therefore, the present invention provides for intermittent incubation of non-pluripotent mammalian cells with one or more of Klf polypeptide, an Oct polypeptide, a Myc polypeptide, and/or a Sox polypeptide, with intervening periods of incubation of the cells in the absence of the one or more polypeptides. In some embodiments, the cycle of incubation with and without the polypeptides can be repeated for 2, 3, 4, 5, 6, or more times and is performed for sufficient lengths of time (i.e., the incubations with and without proteins) to achieve the development of pluripotent cells. Various agents (e.g., MEK inhibitor and/or GSK inhibitor and/or TGFbeta inhibitor) can be included to improve efficiency of the method.

In some embodiments, the non-pluripotent cells are cultured according to a two-step procedure: (1) the cells are first contacted with one or more exogenous polypeptides of the present invention, (2) followed by culturing the cell in the absence of the exogenous polypeptides. This procedure can be repeated for at least two or more cycles, e.g., 2, 3, 4, 5, 10, or more cycles. Each step can be performed for sufficient lengths of time to achieve the pluripotency in the cells. For example, the first step (i.e., incubation in the presence of exogenous polypeptides) can be performed for 1, 2, 5, 12, 24, 36, 48 hours, or longer. The length of time for treatment depends, in part, on the concentrations and activities of the polypeptides used. Similarly, the second step (i.e., culturing the cell in the absence of the exogenous polypeptides) can be performed for 1, 2, 5, 12, 24, 36, 48 hours, or longer. In some embodiments, the non-pluripotent cells are cultured in the presence of one or more exogenous polypeptides of the present invention once per day or as needed. For example, the cells can be cultured in the presence of the exogenous polypeptides overnight, and then cultured in the absence of the exogenous polypeptides for as long as 36 hours. This procedure can be repeated for, e.g., 4 times.

Concentrations of the exogenous polypeptides may vary as needed, e.g., depending on how active the polypeptides are, or whether or not the cells endogenously express the corresponding transcription factors. In some embodiments, the concentration of the polypeptides are at least 0.1 µg/ml, e.g., at least 0.2 µg/ml, 0.5 µg/ml, 1 µg/ml, 5 µg/ml, 10 µg/ml, 100 µg/ml, or 1000 µg/ml; e.g., between 0.1 µg/ml and 1 µg/ml, between 1 µg/ml and 5 µg/ml, between 5 µg/ml and 10 µg/ml, between 10 µg/ml and 100 µg/ml, between 100 µg/ml and 1000 µg/ml. In some embodiments, the concentration of the polypeptides is 8 µg/ml.

As discussed above, the non-pluripotent cells can be cultured in the presence of a protein delivery agent, e.g., a single-wall nanotube or a Profect protein delivery reagent. In some embodiments, the non-pluripotent cells are cultured in the absence of such protein delivery agents. For example, the non-pluripotent cells are contacted with one or more exogenous polypeptides of the present invention in the absence of a lipid, a single-wall nanotube or a Profect protein delivery reagent (e.g., Profect-P1 or Profect-P2).

E. Small Molecules

In addition to exogenous polypeptides, in some embodiments, small molecules can be included. Small molecules include (1) agents that can "complement" or replace what is generally otherwise understood as a necessary expression of one of these proteins to result in pluripotent cells; and/or (2) agents that can improve the efficiency of a process for generating pluripotent cells (e.g., iPS cells). By contacting a cell with an agent that functionally replaces one of the transcription factor, it is possible to generate pluripotent cells with all of the above-listed transcription factors except for the transcription factor replaced or complemented by the agent. Further, in some embodiments, small molecules can improve the efficiency of a process for generating pluripotent cells (e.g., iPS cells). For example, improved efficiency can be manifested by speeding the time to generate such pluripotent cells (e.g., by shortening the time to development of pluripotent cells by at least a day compared to a similar or same process without the small molecule). Alternatively, or in combination, a small molecule can increase the number of pluripotent cells generated by a particular process (e.g., increasing the number in a given time period by at least 10%, 30%, 50%, 100%, 200%, 500%, etc. compared to a similar or same process without the small molecule).

Induction of pluripotent stem cell can comprise a step of contacting the non-pluripotent cell with one or more of small molecules. For example, in some embodiments, mammalian non-pluripotent cells are induced to pluripotency by (a) contacting the non-pluripotent cell with one or more different exogenous polypeptides of the present invention under conditions to produce the induced pluripotent stem cell from the mammalian non-pluripotent cells; and (b) contacting the cells with one or more of an agent that inhibits H3K9 methylation, an L-type Ca channel agonist; an activator of the cAMP pathway; a DNA methyltransferase (DNMT) inhibitor; a nuclear receptor ligand; a GSK3 inhibitor; a MEK inhibitor, a TGFβ receptor/ALK5 inhibitor, a HDAC inhibitor; or an Erk inhibitor, thereby producing induced pluripotent stem cells. In some embodiments, a non-pluripotent cell is induced to pluripotency in a method comprising contacting the non-pluripotent cells with two, three, four, five, six, seven, eight, nine, or each of a MEK inhibitor, an L-type Ca channel agonist; an agent that inhibits H3K9 methylation, an activator of the cAMP pathway; a DNA methyltransferase (DNMT) inhibitor; a nuclear receptor ligand; a GSK3 inhibitor; a TGFβ receptor/ALK5 inhibitor, a HDAC inhibitor; or an Erk inhibitor, wherein each compound is included in an amount sufficient in improve the efficiency of induction. In some embodiments as described in this paragraph, Oct4 only, Oct4/Klf4 only, Sox2/Klf4 only, or one, two, three or four of an Oct polypeptide, a Klf polypeptide, a Socx polypeptide and a Myc polypeptide are further exogenously in the non-pluripotent cells resulting in induction of pluripotency following contacting with agents as described herein.

i. An Agent that Inhibits H3K9 Methylation

Agents that inhibit H3K9 methylation include agents that inhibit methylates (also known as methyl transferases) that target H3K9. For example, G9a histone methyltransferase methylates H3K9 and inhibition of G9a histone methyltransferase is known to reduce methylation of H3K9. See, e.g., Kubicek, et al., *Mol. Cell.* 473-481 (2007). An example of a G9a histone methyltransferase useful according to the methods of the invention is BIX01294 (see, e.g., Kubicek, et al., *Mol. Cell* 473-481 (2007)), or salts, hydrates, isoforms, racemates, solvates and prodrug forms thereof. Bix01294 is displayed below:

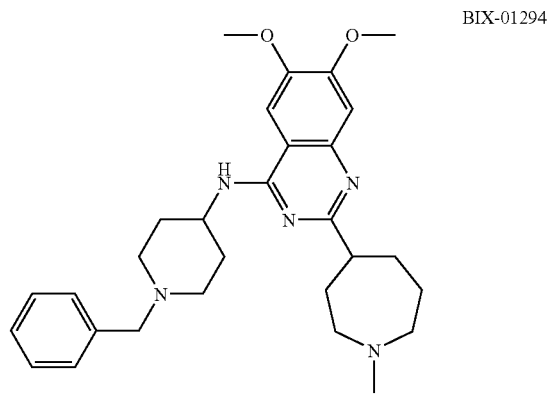 [SMILES: COc1cc2nc(C3CCCN(C)CC3)nc(NC3CCN(Cc4ccccc4)CC3)c2cc1OC]

BIX-01294

The Bix01294 compounds of the present invention also include the salts, hydrates, solvates and prodrug forms. Bix01294 possesses asymmetric carbon atoms (optical centers) or double bonds; the racemates, diastereomers, geometric isomers and individual isomers are all intended to be encompassed within the scope of the present invention. For example, the compound of the present invention can be the R-isomer or the S-isomer, or a mixture thereof. In addition, the compound of the present invention can be the E-isomer or the Z-isomer, or a combination thereof.

In some embodiments, the agent that inhibits H3K9 methylation is a substrate analog of a histone methyl transferase. The substrate of a number of methyl transferases is S-adenosyl-methionine (SAM). Thus, in some embodiments, the agent that inhibits H3K9 methylation is a SAM analog. Exemplary SAM analogs include, but are not limited to, methylthio-adenosine (MTA), sinefungin, and S-adenosyl-homocysteine (SAH). In other embodiments, the agent that inhibits H3K9 methylation does not compete with SAM on a histone methyl transferase.

In other embodiments, BIX01294, or other agents that inhibit H3K9 methylation or promote H3K9 demethylation can be used to induce pluripotency in cells that were previously not pluripotent. In some embodiments, an agent that inhibits H3K9 methylation is used to induce Oct4 expression in cells, or at least alterations in Oct4 promoter DNA methylation and/or histone methylation to allow for induction of cells into pluripotency. Thus, in some embodiments, cells that are not initially pluripotent cells are contacted with an agent that inhibits H3K9 methylation to induce the cells to become pluripotent. Indeed, without intending to limit the scope of the invention to a particular mode of action, the inventors believe that contacting non-pluripotent cells with an agent that inhibits H3K9 methylation or promotes H3K9 demethylation will improve any method of inducing cells to pluripotency. For example, the agent that inhibits H3K9 methylation can be contacted to a non-pluripotent cell and induced to pluripotency in a method comprising contacting the non-pluripotent cells with an agent that inhibits H3K9 methylation, optionally also contacting the cells with one or more of an L-type Ca channel agonist; an activator of the cAMP pathway; a DNA methyltransferase (DNMT) inhibitor; a nuclear receptor ligand; a GSK3 inhibitor; a MEK inhibitor, a TGFβ receptor/ALK5 inhibitor, a HDAC inhibitor; or an Erk inhibitor, wherein each compound is included in an amount sufficient in improve the efficiency of induction. In some embodiments as described in this paragraph, Oct4 only, or Oct4/Klf4, or Sox2/Klf4 are further heterologously expressed in the non-pluripotent cells resulting in induction of pluripotency following contacting with agents as described herein.

ii. L-Type Calcium Channel Agonists

Exemplary L-type calcium channel agonists include, but are not limited to, BayK8644 (see, e.g., Schramm, et al., *Nature* 303:535-537 (1983)), Dehydrodidemnin B (see, e.g., U.S. Pat. No. 6,030,943), FPL 64176 (FPL) (see, e.g., Liwang, et al., *Neuropharmacology* 45:281-292 (2003)), S(+)-PN 202-791 (see, e.g., Kennedy, et al., *Neuroscience* 49:937-44 (1992)) and CGP 48506 (see, e.g., Chahine, et al., *Canadian Journal of Physiology and Pharmacology* 81:135-141 (2003)).

iii. Activators of the cAMP Pathway

Exemplary activators of the cAMP pathway include, but are not limited to, forskolin (see, e.g., Liang, et al., *Endocrinology* 146: 4437-4444 (2005)), FSH (see, Liang, supra), milrinone (see, Liang, supra), cilostamide (see, Liang, supra), rolipram (see, Liang, supra), dbcAMP (see, Liang, supra) and 8-Br-cAMP (see, Liang, supra).

iv. DNA Methyltransferase (DNMT) Inhibitors

Exemplary DNA methyltransferase (DNMT) inhibitors can include antibodies that bind, dominant negative variants of, and siRNA and antisense nucleic acids that suppress expression of DNMT. DNMT inhibitors include, but are not limited to, RG108 (available, e.g., from Sigma-Aldrich), 5-aza-C (5-azacitidine or azacitidine) (see, e.g., Schermelleh, et al., *Nature Methods* 2:751-6 (2005)), 5-aza-2'-deoxycytidine (5-aza-CdR) (see, e.g., Zhu, *Clinical Medicinal Chemistry* 3(3):187-199 (2003)), decitabine (see, e.g., Gore, *Nature Clinical Practice Oncology* 2:S30-S35 (2005)), doxorubicin (see, e.g., Levenson, *Molecular Pharmacology* 71:635-637 (2007)), EGCG ((−)-epigallocatechin-3-gallate) (see, e.g., Fang, et al., *Cancer Research* 63:7563-7570 (2003)), RG108 (see, e.g., Carninci, et al., WO2008/126932, incorporated herein by reference) and zebularine (see, Carninci, supra).

v. Nuclear Receptor Ligands

Exemplary nuclear receptor ligands, i.e., agonists, antagonists, activators and/or repressors of nuclear receptors, can modulate local gene expression or transcription at the site of delivery. Nuclear receptor agonist (and also nuclear receptor antagonists) can be used. In some embodiments, nuclear receptors are co-regulators of transcription. Activation or inhibition of certain nuclear receptors regulate epigenetic states of specific gene loci where they bind. The inventors have found that dexamethasone (e.g., at 1 µM, a glucocorticoid receptor agonist), ciglitazone and Fmoc-Leu (both used at 5 µM) (a PPAR agonist), and Bexarotene (e.g., at (3 µM) (a RXR antagonist) can enhance cellular reprogramming. Representative nuclear receptor ligands include, but are not limited to, estradiol (e.g., 17-beta estradiol), all-trans retinoic acid, 13-cis retinoic acid, dexamethasone, clobetasol, androgens, thyroxine, vitamin D3 glitazones, troglitazone, pioglitazone, rosiglitazone, prostaglandins, and fibrates (e.g., bezafibrate, ciprofibrate, gemfibrozil, fenofibrate and clofibrate). Furthermore, the activity of endogenous ligands (such as the hormones estradiol and testosterone) when bound to their cognate nuclear receptors is normally to upregulate gene expression. This upregulation or stimulation of gene expression by the ligand can be referred to as an agonist response. The agonistic effects of endogenous hormones can also be mimicked by certain synthetic ligands, for example, the glucocortocoid receptor anti-inflammatory drug dexamethasone. Agonist ligands function by inducing a conformation of the receptor which favors coactivator binding. See, e.g., WO08011093A incorporate herein by reference.

vi. GSK3 Inhibitors

Inhibitors of GSK3 can include antibodies that bind, dominant negative variants of, and siRNA and antisense nucleic acids that target GSK3. Specific examples of GSK3 inhibitors include, but are not limited to, Kenpaullone, 1-Azakenpaullone, CHIR99021, CHIR98014, AR-A014418 (see, e.g., Gould, et al., *The International Journal of Neuropsychopharmacology* 7:387-390 (2004)), CT 99021 (see, e.g., Wagman, *Current Pharmaceutical Design* 10:1105-1137 (2004)), CT 20026 (see, Wagman, supra), SB216763 (see, e.g., Martin, et al., *Nature Immunology* 6:777-784 (2005)), AR-A014418 (see, e.g., Noble, et al., *PNAS* 102:6990-6995 (2005)), lithium (see, e.g., Gould, et al., *Pharmacological Research* 48: 49-53 (2003)), SB 415286 (see, e.g., Frame, et al., *Biochemical Journal* 359:1-16 (2001)) and TDZD-8 (see, e.g., Chin, et al., *Molecular Brain Research*, 137(1-2):193-201 (2005)). Further exemplary GSK3 inhibitors available from Calbiochem (see, e.g., Dalton, et al., WO2008/094597, herein incorporated by reference), include but are not limited to BIO (2'Z, 3'£)-6-Bromoindirubin-3'-oxime (GSK3 Inhibitor IX); BIO-Acetoxime (2'Z,3'E)-6-Bromoindirubin-3'-acetoxime (GSK3 Inhibitor X); (5-Methyl-1H-pyrazol-3-yl)-(2-phenylquinazolin-4-yl)amine (GSK3-Inhibitor XIII); Pyridocarbazole-cyclopenadienylruthenium complex (GSK3 Inhibitor XV); TDZD-8 4-Benzyl-2-methyl-1,2,4-thiadiazolidine-3,5-dione (GSK3beta Inhibitor I); 2-Thio(3-iodobenzyl)-5-(1-pyridyl)-[1,3,4]-oxadiazole (GSK3beta Inhibitor II); OTDZT 2,4-Dibenzyl-5-oxothiadiazolidine-3-thione (GSK3beta Inhibitor III); alpha-4-Dibromoacetophenone (GSK3beta Inhibitor VII); AR-AO 14418 N-(4-Methoxybenzyl)-N'-(5-nitro-1,3-thiazol-2-yl)urea (GSK-3beta Inhibitor VIII); 3-(1-(3-Hydroxypropyl)-1H-pyrrolo[2,3-b]pyridin-3-yl]-4-pyrazin-2-yl-pyrrole-2,5-dione (GSK-3beta Inhibitor XI); TWS1 19 pyrrolopyrimidine compound (GSK3beta Inhibitor XII); L803 H-KEAPPAPPQSpP-NH2 (SEQ ID NO:10) or its Myristoylated form (GSK3beta Inhibitor XIII); 2-Chloro-1-(4,5-dibromo-thiophen-2-yl)-ethanone (GSK3beta Inhibitor VI); AR-A0144-18; SB216763; and SB415286. Residues of GSK3b that interact with inhibitors have been identified. See, e.g., Bertrand et al., *J. Mol Biol.* 333(2): 393-407 (2003). GSK3 inhibitors can activate, for example, the Wnt/β-catenin pathway. Many of β-catenin downstream genes co-regulate pluripotency gene networks. For example, a GSK inhibitor activates cMyc expression as well as enhances its protein stability and transcriptional activity. Thus, in some embodiments, GSK3 inhibitors can be used to stimulate endogenous Myc polypeptide expression in a cell, thereby eliminating the need for Myc expression to induce pluripotency.

The inventors have also found that the combination of a GSK inhibitor and an HDAC inhibitor, or a GSK inhibitor and a cAMP pathway activator, or a GSK inhibitor and an ALK5 inhibitor can induce to pluripotency any of mouse or human fibroblasts or keratinocytes that express any of: Oct4 alone, Oct4/Klf4 or Sox2/Klf4. Accordingly, it is believed that cells can also be reprogrammed to pluripotency by introduction of exogenous Oct4 alone, Oct4/Klf4 or Sox2/Klf4 in combination with the small molecules discussed above. In other embodiments, a non-pluripotent cell is induced to pluripotency in a method comprising contacting the non-pluripotent cells with a GSK3 inhibitor, optionally also contacting the cells with one or more of an L-type Ca channel agonist; an activator of the cAMP pathway; a DNA methyltransferase (DNMT) inhibitor; a nuclear receptor ligand; a GSK3 inhibitor; a MEK inhibitor, a TGFβ receptor/ALK5 inhibitor, a HDAC inhibitor; or an Erk inhibitor, wherein each compound is included in an amount sufficient in improve the efficiency of induction. In some embodiments as described in this paragraph, Oct4 only, Oct4/Klf4 only, Sox2/Klf4 only, or one, two, three or four of an Oct polypeptide, a Klf polypeptide, a Socx polypeptide and a Myc polypeptide are further exogenously in the non-pluripotent cells resulting in induction of pluripotency following contacting with agents as described herein.

vii. MEK Inhibitors

In other embodiments, a non-pluripotent cell is induced to pluripotency in a method comprising contacting the non-pluripotent cells with a MEK inhibitor, optionally also contacting the cells with one or more of an L-type Ca channel agonist; an activator of the cAMP pathway; a DNA methyltransferase (DNMT) inhibitor; a nuclear receptor ligand; a GSK3 inhibitor; a TGFβ receptor/ALK5 inhibitor, a HDAC inhibitor; or an Erk inhibitor, wherein each compound is included in an amount sufficient in improve the efficiency of induction. In some embodiments as described in this paragraph, Oct4 only, Oct4/Klf4 only, Sox2/Klf4 only, or one, two, three or four of an Oct polypeptide, a Klf polypeptide, a Socx polypeptide and a Myc polypeptide are further exogenously in the non-pluripotent cells resulting in induction of pluripotency following contacting with agents as described herein.

Inhibitors of MEK can include antibodies to, dominant negative variants of, and siRNA and antisense nucleic acids that suppress expression of, MEK. Specific examples of MEK inhibitors include, but are not limited to, PD0325901, (see, e.g., Rinehart, et al., *Journal of Clinical Oncology* 22: 4456-4462 (2004)), PD98059 (available, e.g., from Cell Signaling Technology), U0126 (available, for example, from Cell Signaling Technology), SL 327 (available, e.g., from Sigma-Aldrich), ARRY-162 (available, e.g., from Array Biopharma), PD184161 (see, e.g., Klein, et al., *Neoplasia* 8:1-8 (2006)), PD184352 (CI-1040) (see, e.g., Mattingly, et al., *The Journal of Pharmacology and Experimental Therapeutics* 316:456-465 (2006)), sunitinib (see, e.g., Voss, et al., US2008004287 incorporated herein by reference), sorafenib (see, Voss supra), Vandetanib (see, Voss supra), pazopanib (see, e.g., Voss supra), Axitinib (see, Voss supra) and PTK787 (see, Voss supra).

Currently, several MEK inhibitors are undergoing clinical trial evaluations. CI-1040 has been evaluate in Phase I and II clinical trials for cancer (see, e.g., Rinehart, et al., *Journal of Clinical Oncology* 22(22):4456-4462 (2004)). Other MEK inhibitors being evaluated in clinical trials include PD184352 (see, e.g., English, et al., *Trends in Pharmaceutical Sciences* 23(1):40-45 (2002)), BAY 43-9006 (see, e.g., Chow, et al., *Cytometry (Communications in Clinical Cytometry)* 46:72-78 (2001)), PD-325901 (also PD0325901), GSK1120212, ARRY-438162, RDEA119, AZD6244 (also ARRY-142886 or ARRY-886), R05126766, XL518 and AZD8330 (also ARRY-704). (See, e.g., information from the National Institutes of Health located on the World Wide Web at clinicaltrials.gov as well as information from the Nation Cancer Institute located on the World Wide Web at cancer.gov/clinicaltrials.

viii. TGF Beta Receptor/ALK5 Inhibitors

In other embodiments, a non-pluripotent cell is induced to pluripotency in a method comprising contacting the non-pluripotent cells with a TGFβ receptor/ALK5 inhibitor, optionally also contacting the cells with one or more of an L-type Ca channel agonist; an activator of the cAMP pathway; a DNA methyltransferase (DNMT) inhibitor; a nuclear receptor ligand; a GSK3 inhibitor; a MEK inhibitor, a HDAC inhibitor; or an Erk inhibitor, wherein each compound is included in an amount sufficient in improve the efficiency of induction. In some embodiments as described in this paragraph, Oct4 only, Oct4/Klf4 only, Sox2/Klf4 only, or one, two, three or four of an Oct polypeptide, a Klf polypeptide, a Socx polypeptide and a Myc polypeptide are further exogenously in the non-pluripotent cells resulting in induction of pluripotency following contacting with agents as described herein.

TGF beta receptor (e.g., ALK5) inhibitors can include antibodies to, dominant negative variants of, and antisense nucleic acids that suppress expression of, TGF beta receptors (e.g., ALK5). Exemplary TGFβ receptor/ALK5 inhibitors include, but are not limited to, SB431542 (see, e.g., Inman, et al., *Molecular Pharmacology* 62(1):65-74 (2002)), A-83-01, also known as 3-(6-Methyl-2-pyridinyl)-N-phenyl-4-(4-quinolinyl)-1H-pyrazole-1-carbothioamide (see, e.g., Tojo, et al., *Cancer Science* 96(11):791-800 (2005), and commercially available from, e.g., Toicris Bioscience); 2-(3-(6-Methylpyridin-2-yl)-1H-pyrazol-4-yl)-1,5-naphthyridine, Wnt3a/BIO (see, e.g., Dalton, et al., WO2008/094597, herein incorporated by reference), BMP4 (see, Dalton, supra), GW788388 (-{4-[3-(pyridin-2-yl)-1H-pyrazol-4-yl]pyridin-2-yl}-N-(tetrahydro-2H-pyran-4-yl)benzamide) (see, e.g., Gellibert, et al., *Journal of Medicinal Chemistry* 49(7):2210-2221 (2006)), SM16 (see, e.g., Suzuki, et al., *Cancer Research* 67(5):2351-2359 (2007)), IN-1130 (3-((5-(6-methylpyridin-2-yl)-4-(quinoxalin-6-yl)-1H-imidazol-2-yl)methyl)benzamide) (see, e.g., Kim, et al., *Xenobiotica* 38(3):325-339 (2008)), GW6604 (2-phenyl-4-(3-pyridin-2-yl-1H-pyrazol-4-yl)pyridine) (see, e.g., de Gouville, et al., *Drug News Perspective* 19(2):85-90 (2006)), SB-505124 (2-(5-benzo[1,3]dioxol-5-yl-2-tert-butyl-3H-imidazol-4-yl)-6-methylpyridine hydrochloride) (see, e.g., DaCosta, et al., *Molecular Pharmacology* 65(3):744-752 (2004)) and pyrimidine derivatives (see, e.g., those listed in Stiefl, et al., WO2008/006583, herein incorporated by reference). Further, while "an ALK5 inhibitor" is not intended to encompass non-specific kinase inhibitors, an "ALK5 inhibitor" should be understood to encompass inhibitors that inhibit ALK4 and/or ALK7 in addition to ALK5, such as, for example, SB-431542 (see, e.g., Inman, et al., *J, Mol. Phamacol.* 62(1): 65-74 (2002). Without intending to limit the scope of the invention, it is believed that ALK5 inhibitors affect the mesenchymal to epithelial conversion/transition (MET) process. TGFβ/activin pathway is a driver for epithelial to mesenchymal transition (EMT). Therefore, inhibiting the TGFβ/activin pathway can facilitate MET (i.e. reprogramming) process.

TGF beta receptor inhibitors can include antibodies to, dominant negative variants of and siRNA or antisense nucleic acids that target TGF beta receptors. Specific examples of inhibitors include but are not limited to SU5416; 2-(5-benzo[1,3]dioxol-5-yl-2-tert-butyl-3H-imidazol-4-yl)-6-methylpyridine hydrochloride (SB-505124); lerdelimumb (CAT-152); metelimumab (CAT-192); GC-1008; ID11; AP-12009; AP-11014; LY550410; LY580276; LY364947; LY2109761; SB-505124; SB-431542; SD-208; SM16; NPC-30345; Ki26894; SB-203580; SD-093; Gleevec; 3,5,7,2',4'-pentahydroxyflavone (Morin); activin-M108A; P144; soluble TBR2-Fc; and antisense transfected tumor cells that target TGF beta receptors. (See, e.g., Wrzesinski, et al., *Clinical Cancer Research* 13(18):5262-5270 (2007); Kaminska, et al., *Acta Biochimica Polonica* 52(2):329-337 (2005); and Chang, et al., *Frontiers in Bioscience* 12:4393-4401 (2007).)

iX. TGFβ/Activin Pathway Inhibitors

In view of the data herein showing the effect of inhibiting ALK5, it is believed that inhibition of the TGFβ/activin pathway will have similar effects. Thus, any inhibitor (e.g., upstream or downstream) of the TGFβ/activin pathway can be used in combination with, or instead of, ALK5 inhibitors as described in each paragraph herein. Exemplary TGFβ/activin pathway inhibitors include but are not limited to: TGF beta receptor inhibitors, inhibitors of SMAD 2/3 phosphorylation, inhibitors of the interaction of SMAD 2/3 and SMAD 4, and activators/agonists of SMAD 6 and SMAD 7. Furthermore, the categorizations described below are merely for organizational purposes and one of skill in the art would know that compounds can affect one or more points within a pathway, and thus compounds may function in more than one of the defined categories.

Inhibitors of SMAD 2/3 phosphorylation can include antibodies to, dominant negative variants of and antisense nucleic acids that target SMAD2 or SMAD3. Specific examples of inhibitors include PD169316; SB203580; SB-431542; LY364947; A77-01; and 3,5,7,2',4'-pentahydroxyflavone (Morin). (See, e.g., Wrzesinski, supra; Kaminska, supra; Shimanuki, et al., *Oncogene* 26:3311-3320 (2007); and Kataoka, et al., EP1992360, incorporated herein by reference.)

Inhibitors of the interaction of SMAD 2/3 and smad4 can include antibodies to, dominant negative variants of and antisense nucleic acids that target SMAD2, SMAD3 and/or smad4. Specific examples of inhibitors of the interaction of SMAD 2/3 and SMAD4 include but are not limited to Trx-SARA, Trx-xFoxH1b and Trx-Lef1. (See, e.g., Cui, et al., *Oncogene* 24:3864-3874 (2005) and Zhao, et al., *Molecular Biology of the Cell,* 17:3819-3831 (2006).)

Activators/agonists of SMAD 6 and SMAD 7 include but are not limited to antibodies to, dominant negative variants of and antisense nucleic acids that target SMAD 6 or SMAD 7. Specific examples of inhibitors include but are not limited to smad7-as PTO-oligonucleotides. (See, e.g., Miyazono, et al., U.S. Pat. No. 6,534,476, and Steinbrecher, et al., US2005119203, both incorporated herein by reference.)

x. HDAC Inhibitors

In some embodiments, one or more small molecules may be supplemented in combination with the exogenous polypeptides when inducing pluripotent stem cell from a mammalian non-pluripotent cell. In some embodiments, a HDAC inhibitor is supplemented in culturing the cells with the exogenous polypeptides. For example, it has been found that valproic acid (VPA) can significantly improve the reprogramming efficiency. In some embodiments, 1 mM VPA is supplemented when culturing the cells with the exogenous polypeptides. In some embodiments, the cells are cultured in the absence of VPA.

In some embodiments, a non-pluripotent cell is induced to pluripotency in a method comprising contacting the non-pluripotent cells with a HDAC inhibitor, optionally also contacting the cells with one or more of an L-type Ca channel agonist; an activator of the cAMP pathway; a DNA methyltransferase (DNMT) inhibitor; a nuclear receptor ligand; a GSK3 inhibitor; a MEK inhibitor, a TGFβ receptor/ALK5 inhibitor, or an Erk inhibitor, wherein each compound is included in an amount sufficient in improve the efficiency of induction.

Exemplary HDAC inhibitors can include antibodies that bind, dominant negative variants of, and siRNA and antisense nucleic acids that target HDAC. HDAC inhibitors include, but are not limited to, TSA (trichostatin A) (see, e.g., Adcock, *British Journal of Pharmacology* 150:829-831 (2007)), VPA (valproic acid) (see, e.g., Munster, et al., *Journal of Clinical Oncology* 25:18 S (2007): 1065), sodium butyrate (NaBu) (see, e.g., Han, et al., *Immunology Letters* 108:143-150 (2007)), SAHA (suberoylanilide hydroxamic acid or vorinostat) (see, e.g., Kelly, et al., *Nature Clinical Practice Oncology* 2:150-157 (2005)), sodium phenylbutyrate (see, e.g., Gore, et al., *Cancer Research* 66:6361-6369 (2006)), depsipeptide (FR901228, FK228) (see, e.g., Zhu, et al., *Current Medicinal Chemistry* 3(3):187-199 (2003)), trapoxin (TPX) (see, e.g., Furumai, et al., *PNAS* 98(1):87-92 (2001)), cyclic hydroxamic acid-containing peptide 1 (CHAP1) (see, Furumai supra), MS-275 (see, e.g., Carninci, et al., WO2008/126932, incorporated herein by reference)), LBH589 (see, e.g., Goh, et al., WO2008/108741 incorporated herein by reference) and PXD 101 (see, Goh, supra). In general at the global level, pluripotent cells have more histone acetylation, and differentiated cells have less histone acetylation. Histone acetylation is also involved in histone and DNA methylation regulation. In some embodiments, HDAC inhibitors facilitate activation of silenced pluripotency genes.

xi. ERK Inhibitors

Exemplary ERK inhibitors include PD98059 (see, e.g., Zhu, et al., *Oncogene* 23:4984-4992 (2004)), U0126 (see, Zhu, supra), FR180204 (see, e.g., Ohori, Drug News Perspective 21(5):245-250 (2008)), sunitinib (see, e.g., Ma, et al., US2008004287 incorporated herein by reference), sorafenib (see, Ma, supra), Vandetanib (see, Ma, supra), pazopanib (see, Ma, supra), Axitinib (see, Ma, supra) and PTK787 (see, Ma, supra).

Once the cells have been contacted with the exogenous polypeptides of the present invention, and/or expression cassettes have been introduced into the cells, and/or the cells have been contacted with the one or more agents, the cells can be optionally screen for characteristics of pluripotent stem cells, thereby identifying those cells in a mixture that are pluripotent. Such cells can be, for example, isolated from the other cells and used further as appropriate.

III. Non Pluripotent Cells

As used herein, "non-pluripotent cells" refer to mammalian cells that are not pluripotent cells. Examples of such cells include differentiated cells as well as progenitor cells. Examples of differentiated cells include, but are not limited to, cells from a tissue selected from bone marrow, skin, skeletal muscle, fat tissue and peripheral blood. Exemplary cell types include, but are not limited to, keratinocyte, hair follicle cells, HUVEC (Human Umbilical Vein Endothelial Cells), cord blood cells, fibroblasts, hepatocytes, myoblasts, neurons, osteoblasts, osteoclasts, and T-cells.

In some embodiments where an individual is to be treated with the resulting pluripotent cells, the individual's own non-pluripotent cells are used to generate pluripotent cells according to the methods of the invention.

Cells can be from, e.g., humans or non-human mammals. Exemplary non-human mammals include, but are not limited to, mice, rats, cats, dogs, rabbits, guinea pigs, hamsters, sheep, pigs, horses, and bovines.

VI. Uses for Pluripotent Cells

The present invention allows for the further study and development of stem cell technologies, including but not limited to, prophylactic or therapeutic uses. For example, in some embodiments, cells of the invention (either pluripotent cells or cells induced to differentiate along a desired cell fate) are introduced into individuals in need thereof, including but not limited to, individuals in need of regeneration of an organ, tissue, or cell type. In some embodiments, the cells are originally obtained in a biopsy from an individual; induced into pluripotency as described herein, optionally induced to differentiate (for examples into a particular desired progenitor cell) and then transplanted back into the individual. In some embodiments, the cells are genetically modified prior to their introduction into the individual.

In some embodiments, the pluripotent cells generated according to the methods of the invention are subsequently induced to form, for example, hematopoietic (stem/progenitor) cells, neural (stem/progenitor) cells (and optionally, more differentiated cells, such as subtype specific neurons, oligodendrocytes, etc), pancreatic cells (e.g., endocrine progenitor cell or pancreatic hormone-expressing cells), hepatocytes, cardiovascular (stem/progenitor) cells (e.g., cardiomyocytes, endothelial cells, smooth muscle cells), retinal cells, etc.

A variety of methods are known for inducing differentiation of pluripotent stem cells into desired cell types. A non-limiting list of recent patent publications describing methods for inducing differentiation of stem cells into various cell fates follows: U.S. Patent Publication No. 2007/0281355; 2007/0269412; 2007/0264709; 2007/0259423; 2007/0254359; 2007/0196919; 2007/0172946; 2007/0141703; 2007/0134215.

A variety of diseases may be ameliorated by introduction, and optionally targeting, of pluripotent cells of the invention to a particular injured tissue. Examples of disease resulting from tissue injury include, but are not limited to, neurodegeneration disease, cerebral infarction, obstructive vascular disease, myocardial infarction, cardiac failure, chronic obstructive lung disease, pulmonary emphysema, bronchitis, interstitial pulmonary disease, asthma, hepatitis B (liver damage), hepatitis C (liver damage), alcoholic hepatitis (liver damage), hepatic cirrhosis (liver damage), hepatic insufficiency (liver damage), pancreatitis, diabetes mellitus, Crohn disease, inflammatory colitis, IgA glomerulonephritis, glomerulonephritis, renal insufficiency, decubitus, burn, sutural wound, laceration, incised wound, bite wound, dermatitis, cicatricial keloid, keloid, diabetic ulcer, arterial ulcer and venous ulcer.

The polypeptides described herein (e.g., one or more of a Klf polypeptide, an Oct polypeptide, a Myc polypeptide, and a Sox polypeptide) are themselves useful therapeutic agents alone, or in combination as described herein. For example, the polypeptides, or combinations thereof, are useful for reducing tissue damage and thus can be administered to treat, ameliorate, or prevent tissue damage. In some embodiments, a compound of the invention is administered to an individual having, or at risk of having tissue damage to an internal organ. Internal organs include, but are not limited to, brain, pancreas, liver, intestine, lung, kidney, or heart, wounding, e.g., by burn or cut. For example, in some embodiments, the compounds of the invention are effective in reducing infarction size in reperfusion following ischemia. Thus, a protein of the invention can be administered to individuals at risk of having, having, or who have had, a stroke. Similarly, a protein of the invention can be administered to individuals at risk of having, having, or who have had, a heart attack or cardiac damage.

The agents described herein (e.g., an agent that inhibits H3K9 methylation; an L-type Ca channel agonist; an activator of the cAMP pathway; a DNA methyltransferase (DNMT) inhibitor; a nuclear receptor ligand; a GSK3 inhibitor; a MEK inhibitor, a TGFβ receptor/ALK5 inhibitor, a HDAC inhibitor; or an Erk inhibitor) are also useful therapeutic agents in combination with the polypeptides as described herein. For example, the agents in combination with the polypeptides are useful for reducing tissue damage and thus can be administered to treat, ameliorate, or prevent tissue damage. In some embodiments, an agent in combination with the polypeptides of the invention is administered to an individual having, or at risk of having tissue damage to an internal organ. Internal organs include, but are not limited to, brain, pancreas, liver, intestine, lung, kidney, or heart, wounding, e.g., by burn or cut. For example, in some embodiments, the agents in combination with the polypeptides of the invention are effective in reducing infarction size in reperfusion following ischemia. Thus, an agent in combination with the polypeptides of the invention can be administered to individuals at risk of having, having, or who have had, a stroke. Similarly, an agent in combination with the polypeptides of the invention can be administered to individuals at risk of having, having, or who have had, a heart attack or cardiac damage.

Active compounds described herein also include the salts, hydrates, solvates and prodrug forms thereof. The compounds of the present invention also include the isomers and metabolites thereof. Certain compounds of the present invention possess asymmetric carbon atoms (optical centers) or double bonds; the racemates, diastereomers, geometric isomers and individual isomers are all intended to be encompassed within the scope of the present invention. For example, the compound of the present invention can be the R-isomer or the S-isomer, or a mixture thereof. In addition, the compound of the present invention can be the E-isomer or the Z-isomer, or a combination thereof.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts. In some embodiments, the present invention provides the hydrochloride salt. In other embodiments, the compound is ellipticine hydrochloride.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds can be regenerated by contacting the salt with a base or acid and isolating the parent compound in the conventional manner. The parent form of the compound can differ from the various salt forms in certain physical properties, such as solubility in polar solvents, but otherwise the salts are equivalent to the parent form of the compound for the purposes of the present invention.

The compounds of the present invention can be made by a variety of methods known to one of skill in the art (see *Comprehensive Organic Transformations* Richard C. Larock, 1989). One of skill in the art will appreciate that other methods of making the compounds are useful in the present invention.

Administration of cells or compounds described herein is by any of the routes normally used for introducing pharmaceuticals. The pharmaceutical compositions of the invention may comprise a pharmaceutically acceptable carrier. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., *Remington's Pharmaceutical Sciences*, $17^{th}$ ed. 1985)).

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, intrathecally or into the eye (e.g., by eye drop or injection). The formulations of compounds can be presented in unit-dose or multi-dose sealed containers, such as ampoules and vials. Solutions and suspensions can be prepared from sterile powders, granules, and tablets of the kind previously described. The modulators can also be administered as part of a prepared food or drug.

The dose administered to a patient, in the context of the present invention should be sufficient to induce a beneficial response in the subject over time, i.e., to ameliorate a condition of the subject. The optimal dose level for any patient will depend on a variety of factors including the efficacy of the specific modulator employed, the age, body weight, physical activity, and diet of the patient, and on a possible combination with other drug. The size of the dose also will be determined by the existence, nature, and extent of any adverse side-effects that accompany the administration of a particular compound or vector in a particular subject. Administration can be accomplished via single or divided doses.

VIII. Cell Mixtures

As discussed herein, the present invention provides for mammalian non-pluripotent cells in a mixture with one or more different exogenous polypeptides of the present invention. The exogenous polypeptides comprise a transcription factor fused to a heterologous peptide sequence that enhances transport across cell membranes. The mixture can have one, two, three, four or more transcription factors, e.g., a transcription factor selected from the group consisting of a Klf polypeptide, an Oct polypeptide, a Myc polypeptide, and a Sox polypeptide. In some embodiments, the mixture of the present invention comprises mammalian non-pluripotent cells and a first exogenous polypeptide comprising a first transcription factor selected from a Klf polypeptide, an Oct polypeptide, a Myc polypeptide, and a Sox polypeptide. A mixture according to the present invention can further contain a second, third, and fourth exogenous polypeptides, for example, exogenous polypeptides comprising a second, third, or fourth transcription factor selected from a Klf polypeptide, an Oct polypeptide, a Myc polypeptide, and a Sox polypeptide, wherein the second, third and fourth polypeptides are different from each other and different from the first polypeptide. In some embodiments, the mixture contain three exogenous polypeptides (e.g., a Klf polypeptide, an Oct polypeptide, and a Sox polypeptide) but not other transcription factors (e.g., a Myc polypeptide).

In some embodiments, the mixture of the present invention further comprises an additional transcription factor other than a Klf polypeptide, an Oct polypeptide, a Myc polypeptide, and a Sox polypeptide. In some embodiments, the additional transcription factor is a Nanog polypeptide. In some embodiments, the additional transcription factor is not a Nanog polypeptide, i.e., the mixture of the present invention does not contain a Nanog polypeptide.

As discussed herein, the present invention also provides for non-pluripotent cells in a mixture with one or more different exogenous polypeptides, and further with one or more compound selected from the group consisting of an agent that inhibits H3K9 methylation, an L-type Ca channel agonist; an activator of the cAMP pathway; a DNA methyltransferase (DNMT) inhibitor; a nuclear receptor ligand; a GSK3 inhibitor; a MEK inhibitor, a TGFβ receptor/ALK5 inhibitor, a HDAC inhibitor; or an Erk inhibitor. In some embodiments, the mixture comprises a combination of one or more compound as described herein, e.g., a combination of a TGFβ receptor/ALK5 inhibitor and a MEK inhibitor; a combination of a TGFβ receptor/ALK5 inhibitor and a GSK3 inhibitor; and a combination of a TGFβ receptor/ALK5 inhibitor, a GSK3 inhibitor, and a MEK inhibitor; etc. In some embodiments, the compound is in the mixture at a concentration sufficient to induce or improve efficiency of induction to pluripotency. For example, in some embodiments, the compounds are in a concentration of at least 0.1 nM, e.g., at least 1, 10, 100, 1000, 10000, or 100000 nM, e.g., between 0.1 nM and 100000 nM, e.g., between 1 nM and 10000 nM, e.g., between 10 nM and 10000 nM. In some embodiments, the mixtures are in a synthetic vessel (e.g., a test tube, Petri dish, etc.). Thus, in some embodiments, the cells are isolated cells (not part of an animal). In some embodiments, the cells are isolated from an animal (human or non-human), placed into a vessel, contacted with one or more compound as described herein. The cells can be subsequently cultured and optionally, inserted back into the same or a different animal, optionally after the cells have been stimulated to become a particular cell type or lineage.

Examples of non-pluripotent cells include those described herein, including but not limited to, cells from a tissue selected from bone marrow, skin, skeletal muscle, fat tissue and peripheral blood. Exemplary cell types include, but are not limited to, keratinocyte, hair follicle cells, HUVEC (Human Umbilical Vein Endothelial Cells), cord blood cells, fibroblasts, hepatocytes, myoblasts, neurons, osteoblasts, osteoclasts, and T-cells.

IX. Kits

The present invention also provides kits, e.g., for use in inducing or improving efficiency of induction of pluripotency in cells. Such kits can comprise at least one exogenous polypeptides of the present invention. The exogenous polypeptides comprise a transcription factor fused to a heterologous peptide sequence that enhances transport across cell membranes. The kit can have one, two, three, four or more transcription factors, e.g., a transcription factor selected from the group consisting of a Klf polypeptide, an Oct polypeptide, a Myc polypeptide, and a Sox polypeptide. In some embodiments, the kit of the present invention comprises a first exogenous polypeptide comprising a first transcription factor selected from a Klf polypeptide, an Oct polypeptide, a Myc polypeptide, and a Sox polypeptide. A kit according to the present invention can further contain a second, third, and fourth exogenous polypeptides, for example, exogenous polypeptides comprising a second, third, or fourth transcription factor selected from a Klf polypeptide, an Oct polypeptide, a Myc polypeptide, and a Sox polypeptide, wherein the second, third and fourth polypeptides are different from each other and different from the first polypeptide.

In some embodiments, the kit of the present invention further comprises an additional transcription factor other than a Klf polypeptide, an Oct polypeptide, a Myc polypeptide, and a Sox polypeptide. In some embodiments, the additional transcription factor is not Nanog, i.e., the kit of the present invention does not contain a Nanog polypeptide.

As discussed herein, the present invention also provides kits comprising one or more different exogenous polypeptides, and further comprising one of more compound selected from the group consisting of an agent that inhibits H3K9 methylation; an L-type Ca channel agonist; an activator of the cAMP pathway; a DNA methyltransferase (DNMT) inhibitor; a nuclear receptor ligand; a GSK3 inhibitor; a MEK inhibitor, a TGFβ receptor/ALK5 inhibitor, a HDAC inhibitor; or an Erk inhibitor.

In some embodiments, the kits further comprise non-pluripotent cells. Examples of non-pluripotent cells include those described herein, including but not limited to, cells from a tissue selected from bone marrow, skin, skeletal muscle, fat tissue and peripheral blood. Exemplary cell types include, but are not limited to, keratinocyte, hair follicle cells, HUVEC (Human Umbilical Vein Endothelial Cells), cord blood cells, fibroblasts, hepatocytes, myoblasts, neurons, osteoblasts, osteoclasts, and T-cells.

EXAMPLE

Example 1

This example demonstrates that incubation of mammalian cells with transcription factor proteins is sufficient to induce pluripotency.

Gene Construction:

In order to obtain the high level protein expression in *E. coli*, all four human TF gene codon region were optimized first (G A Gutman and G W Hatfield (1989). PNAS. vol. 86. pp:3699-3703), and full-length synthesized using DNA oligo based/PCR gene assembling technology (Danilo R Casimiro, Peter E Wright & H Jane Dyson. (1997). Structure. Vol. 5. pp: 1407-1412.). Poly-arginine tag: ESGGGGSPGR-RRRRRRRRRR (SEQ ID NO:2) was added to each protein C-terminal in design (Gump J M, Dowdy S F. (2007) Trends Mol Med. 2007 October; 13(10):443-8). The final DNA fragment was flanked with NdeI and XhoI site, and inserted into pET41 expression vector NdeI-XhoI sites for protein expression. Each plasmid were verified with DNA sequence, then transformed into BL21start competent cells for recombinant protein production using auto-induction medium overnight (Studier F W, (2005) Protein Expr Purif. 41(1). Pp: 207-234.).

Protein Preparation

*Escherichia coli* BL21(DE3) cells were transformed with pET-Oct4-PTD ("PTD" refers to protein transduction domain), pET-Sox2-PTD, pET-Klf4-PTD, and pET-c-Myc-PTD separately, and the protein expression was done using the auto-induction method (Studier F. W., Protein Expression and Purification, 41 (2005) 207-234). Inclusion bodies were solubilized and the proteins were refolded as described (LaFevre B M, Wu S. & Lin X. Molecular Cancer Therapeutics 7, 1420-1429, Jun. 1, 2008. doi: 10.1158/1535-7163; Medynski D., Tuan M., Liu, W., Wu, S. & Lin, X. Protein Expression and Purification Vol. 52, 395-402, April 2007; Hou W., Medynski D., Wu, S., Lin, X. & Li, L Y. Clinical Cancer Research Vol. 11, 5595-5602, Aug. 1, 2005).

Briefly, *E. coli* containing an expression plasmid was inoculated into 1.0 L liter of Luria-Bertani Broth containing kanamycin, induced with 500 umol/L IPTG at A600 nm=0.6, and agitated for 3 hours at 37 C. The cells were collected by centrifugation, and the pellet subjected to freeze- and thaw cycles. The inclusion bodies released were washed extensive with a buffer containing 20 mmol/L tris, 100 mmol/L NaCl, 1% TritonX-100 (pH8.0) and dissolved in a buffer containing 8 mol/L urea, 0.1 mol/L Tris, 1 mmol/L glycine, 1 mmol/L EDTA, 10 mmol/L b-mercaptoethanol, 10 mmol/L DTT, 1 mmol/L reduced glutathione, 0.1 mmol/L oxidized glutathione (pH 10) with a A280 nm=2.0. The solubilized inclusion bodies were refolded with a rapid dilution method as described (Lin X L, Lin Y Z, Tang J., Methods Enzymol 1994, 241, 195-224; Lin X, Koelsh G., Wu. S, Downs D, Dashti A. Tang J. Proc Natl Acad Sci USA. 2000; 97. 1556-1560; Kim Y T. Downs D. Wu S, et al. Eur J Biochem 2002, 269: 5669-77; Michelle LaFevre-Bernt, Shili Wu, and Xinli Lin. (2008). Molecular Cancer Therapeutics. 7: pp:1420-1429). The refolded protein was concentrated by N2-ultrafiltration and purified by size exclusion chromatography using Sephacryl S 300. The endotoxin concentration in each of protein preparation was less than 100 EU/mg. Most refold protein samples have solubility at least >1.5 mg/ml.

Refolded proteins were concentrated using tangential flow filtration, purified using size exclusion chromatography with a Superdex-200 column (XK26×850-mm, GE, Piscataway, N.J.), and confirmed using SDS-PAGE.

Mouse fibroblasts were grown in mESC medium supplemented with 8 μg/ml of either Oct4/Sox2/Klf4 or Oct4/Sox2/Klf4/Myc (all proteins comprising poly-Arg as described above) for 6-8 hours, washed, and incubated for 2-3 days in mESC media without the above-listed transcription factors. This (4-12 hours with, 1-3 days without) was repeated a number (1, 2, 3, 4, or more) of times and then the cells were cultures in mESC for two weeks. At the end of this period, the cultures were determined to contain pluripotent cells by colony morphology and marker expression. Notably, it was found that constant incubation of the cells with the transcription factors (i, e., without the 1-3 day period without the proteins)) was toxic to the cells. While it was not necessary, the cells were sometimes incubated with MEK inhibitor (PD0325901) and/or GSK inhibitor (CHIR99021) and/or TGFbeta inhibitor (SB431542) and the presence of these agents improved efficiency and speed of development of pluripotent cells.

Example 2

Ground-breaking work demonstrated that ectopic expression of four transcription factors, Oct4, Klf4, Sox2 and c-Myc could reprogram murine somatic cells to induced pluripotent stem (iPS) cells (Takahashi, K. et al., *Cell*, 131, 861-872 (2007); Yamanaka, S., *Cell*, 137(1) 13-17 (2009)), and human iPS cells were subsequently generated using similar genetic manipulation (Takahashi, K. et al., Cell, 131, 861-872 (2007); Yu, J. et al., *Science*, 318, 1917-1920 (2007)). Here we report generation of protein induced pluripotent stem (piPS) cells from murine embryonic fibroblasts using recombinant cell-penetrating reprogramming proteins. We demonstrated that such piPS cells can long-term self-renew and are pluripotent in vitro and in vivo.

Figure 3:
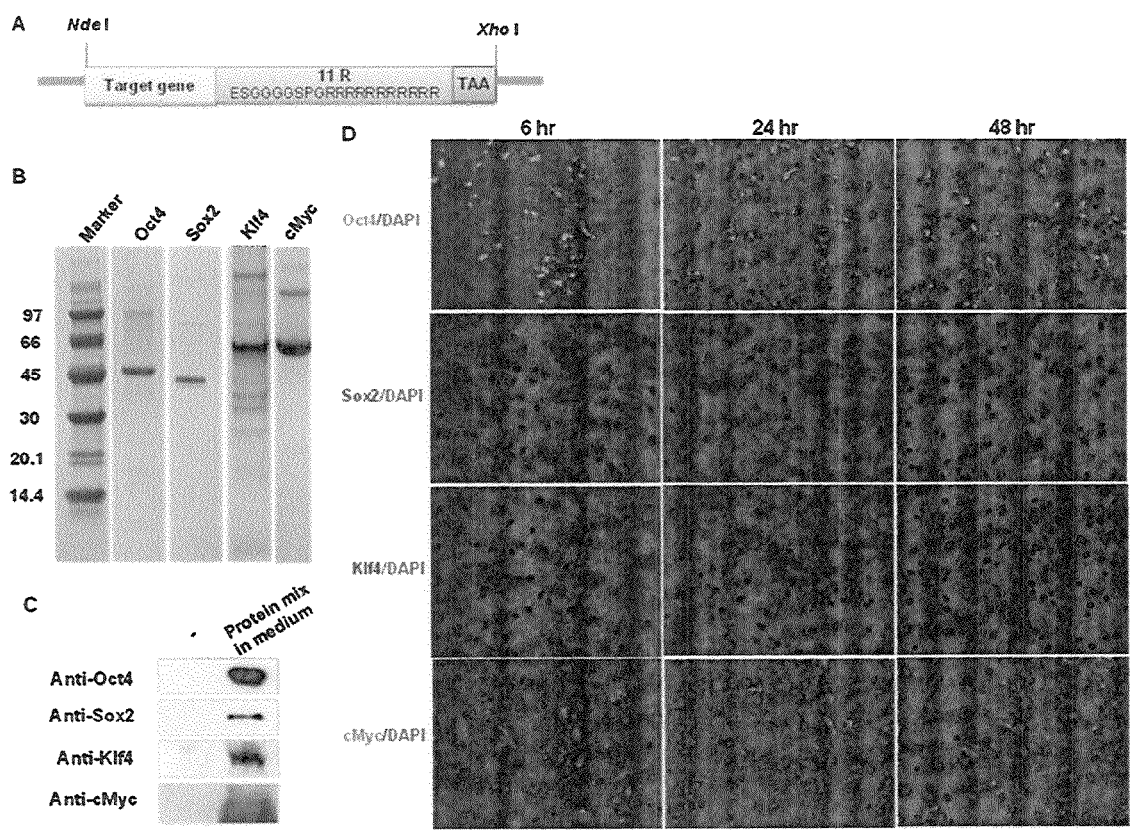
FIG. 3. Characterization of recombinant reprogramming proteins. (A) Schematic of the protein expression vector (SEQ ID NO:2). (B) Following protein refolding and purification, Oct4 (lane 2), Sox2 (lane 3), Klf4 (lane 4), and cMyc (lane 5) were analyzed by 4-12% Bis-Tris NuPage Gel and Coomassie blue staining. The protein standards were shown in lane 1. (C) Stability of the four recombinant reprogramming proteins under the cell culture condition was examined by Western blot analysis. Proteins (8 μg/ml) were added into mESC growth media and incubated at 37° C. for 12 hr. Medium samples were then collected and subjected to Western blot analysis. The specific antibodies against Oct4, Sox2, Klf4, and cMyc were used. (D) Protein transduction of 11R-tagged reprogramming proteins into MEF cells was examined by immunocytochemistry. Eight μg/ml of Oct4, Sox2, Klf4 and cMyc proteins were added to OG2-MEF cells. Cells were cultured for 6 hr, 24 hr and 48 hr, and then fixed and immunostained. Cells were also stained with DAPI to visualize the nuclei and the images were merged.

One possible way to avoid introducing exogenous genetic modifications to target cells would be to deliver the reprogramming proteins directly into cells, rather than relying on the transcription from delivered genes. Previous studies have demonstrated that various proteins can be delivered into cells in vitro and in vivo by conjugating them with a short peptide that mediates protein transduction, such as HIV tat and poly-arginine (Inoue, M. et al., *Eur Urol*, 49, 161-168 (2006); Michiue, H. et al., *J Biol Chem*, 280, 8285-8289 (2005); Wadia, J. S., and Dowdy, S. F., *Curr Opin Biotechnol*, 13, 52-56 (2002)). In addition, various solubilization and refolding techniques for processing inclusion body proteins expressed in *E. coli* to bioactive proteins have been developed to allow facile and large scale production of therapeutic proteins (Lafevre-Bernt, M., Wu, S., and Lin, X., *Mol Cancer Ther*, 7, 1420-1429 (2008)). To generate recombinant proteins that can penetrate across the plasma membrane of somatic cells, we designed and fused a poly-arginine (i.e. 11R) protein transduction domain to the C-terminal of four reprogramming factors: Oct4, Sox2, Klf4 and cMyc (FIG. 3A). These proteins were expressed in *E. Coli* in inclusion bodies, which were then solubilized, refolded, and further purified (FIG. 3B). The protein identities were confirmed by mass spectrometry and Western blot analysis (FIG. 3C).

To test the cell permeability and stability of the proteins, we treated mouse embryonic fibroblast (MEF) cells with the recombinant proteins at various concentrations by adding them to the cell culture media for 6-72 hours, and examining cell morphology and protein presence by immunocytochemistry. We found that the purified 11R tagged recombinant transcription factors readily entered cells at concentrations of 0.5-8 µg/ml within 6 hours, and could translocate into nucleus (FIG. 3D). In addition, we found that the transduced proteins appeared to be stable inside cells for up to 48 hours (FIG. 3D).

We then employed this simple protein transduction protocol to reprogram OG2/Oct4-GFP reporter MEF cells. Because reprogramming through the iPS-cell mechanism/process typically requires sustained activity of reprogramming proteins for 7-10 days, we devised a strategy that involved treating the cells in 4 cycles. In each cycle the fibroblasts (initially seeded at the density of $5 \times 10^4$ cells/well in a six-well plate) were first treated overnight with the recombinant reprogramming proteins (i.e. Oct4-11R, Sox2-11R, Klf4-11R and cMyc-11R) at 8 µg/ml in the mESC growth media supplemented with or without 1 mM valproic acid (VPA), a HDAC inhibitor that can significantly improve reprogramming efficiency (Huangfu, D. et al., *Nat Biotechnol*, 26, 795-797 (2008a)), followed by changing to the same media without the recombinant reprogramming proteins and VPA, and culturing for additional 36 hours before the next cycle of the treatment. After completing four repeated protein transductions of reprogramming proteins, the treated cells were transferred onto irradiated MEF feeder cells and simply kept in mESC growth media until colonies emerged around day 30-35 (FIG. 1A). We obtained 3 $GFP^+$ colonies per $5 \times 10^4$ cells when they were transduced with four proteins and treated with VPA, and 1 $GFP^+$ colony per $5 \times 10^4$ cells when they were transduced with only three proteins (i.e. Oct4-11R, Sox2-11R, and Klf4-11R) and treated with VPA. However, we did not obtain stable $GFP^+$ piPS cell colonies by transducing the three or four reprogramming proteins only for the same period of time, although GFP-negative cell colonies were observed. Those GFP-negative cell colonies stained positive with ALP, an early pluripotency marker, suggesting they might be partially reprogrammed cells. The initial $GFP^+$ colonies were subsequently passaged under conventional mESC growth conditions to yield piPS cells, and were characterized further.

Figure 4:
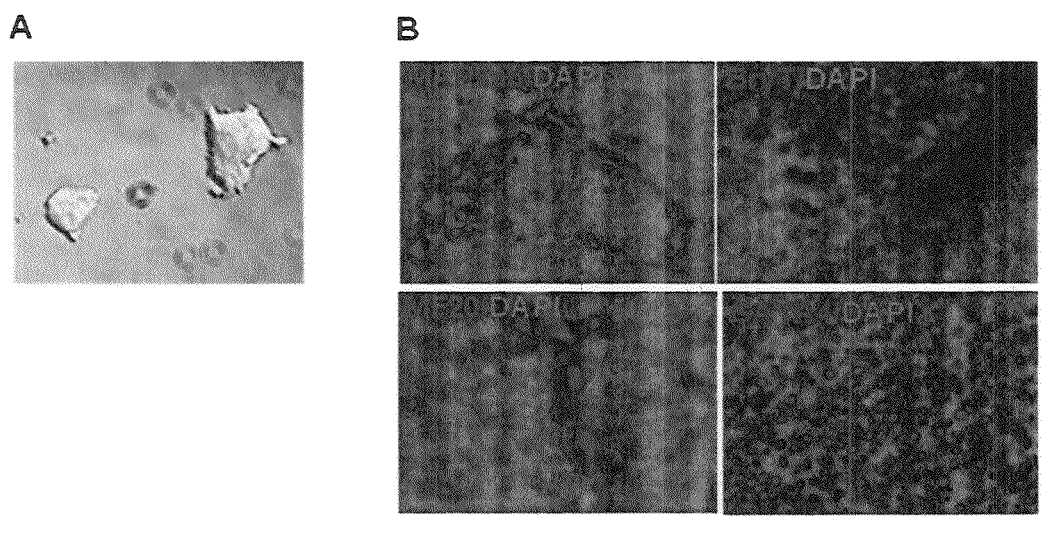
FIG. 4. Additional characterizations of piPS cells. (A) piPS cells clonally expand and self-renew in chemically defined media and feeder free condition. (B) piPS cells can effectively differentiate in vitro into mature neurons (MAP2ab$^+$), BryT$^+$ mesoderm cells, mature cardiomyocytes (MF20$^+$), and GATA4$^+$ endoderm cells. (C) GFP genotyping of chimeric embryos. Five fetuses were randomly picked, including one fetus which showed Oct4-GFP positive cells in the gonad. GFP integration in five different tissues, namely heart, liver, brain, tail and gonad, was analyzed by genomic PCR. Positive detection of GFP sequence in all five tissues of 3 fetuses, in four tissues of one fetus, and in three tissues of one fetus, confirmed that piPS cells could contribute to the three germ layer (mesoderm, endoderm and ectoderm) plus gonad in vivo.

The generated murine piPS cells have been stably and homogenously expanded for over thirty passages, and are morphologically indistinguishable from classic mES cells, forming compact domed small colonies (FIG. 1C). They express typical pluripotency markers by immunocytochemistry and staining, including ALP (FIG. 1D), Oct4, Nanog, Sox2, and SSEA1 (FIG. 1E). RT-PCR analysis confirmed endogenous gene expression of these and additional pluripotency genes (FIG. 1F). A single cell survival assay also demonstrated that piPS cells clonally expand efficiently as Oct4-positive colonies in feeder-free and N2/B27-chemically defined conditions (FIG. 4A). Bisulphite genomic sequencing analyses of the Oct4 and Nanog promoters revealed that both were demethylated in piPS cells as in mES cells, while in MEFs they were hypermethylated (FIG. 1G). This result provides further evidence for reactivation of the pluripotency transcription program in the piPS cells. Global gene expression analysis of piPS cells, OG2-MEFs and mES cells showed that piPS cells are distinct from OG2-MEFs (Pearson correlation value: 0.895) and most similar to mES cells (Pearson correlation value: 0.969) (FIG. 1H), consistent with previous reports.

Figure 2:
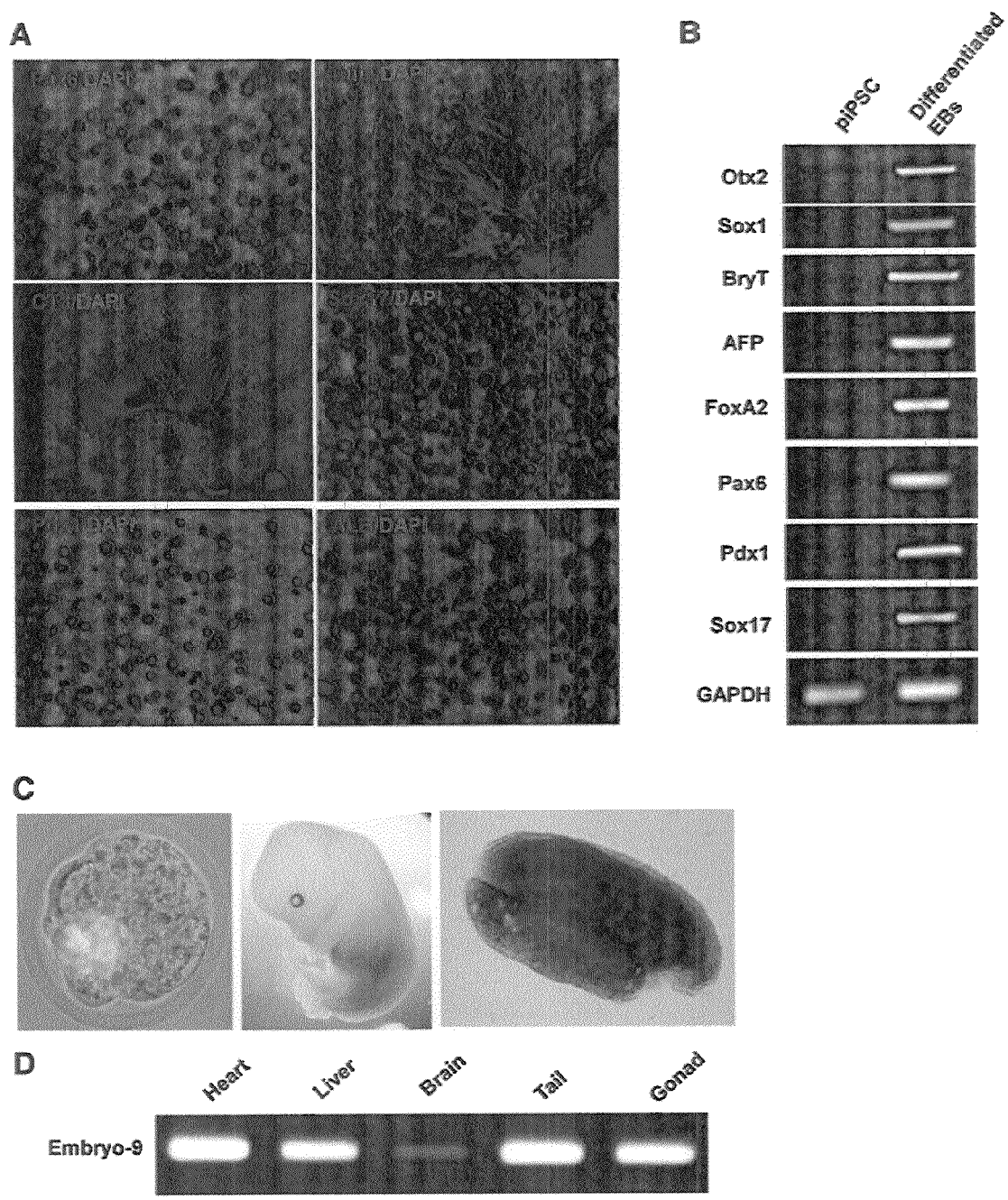
FIG. 2. In vitro and in vivo pluripotency of piPS cells. (A) piPS cells can effectively differentiate in vitro into cells in the three germ layers, including neural progenitor cells (Pax6$^+$), characteristic neurons (TUJ1$^+$), mature cardiomyocytes (CT3$^+$), definitive endoderm cells (Sox17$^+$), pancreatic cells (Pdx1$^+$), and hepatic cells (ALB$^+$). Images were merged with DAPI staining (B) RT-PCR analysis of in vitro differentiation of piPS cells. (C) piPSCs incorporate into the ICM of the blastocytes after aggregation with eight-cell embryos (left). Chimeric fetuses (13.5 dpc, middle) were obtained after transfer of the piPS cell aggregated embryos into pseudo-pregnant mice. piPS cells contributed to the germline cells (Oct4-GFP positive) in isolated genital ridge tissue from chimeric fetuses (found in 3 out of 17 fetuses, right). (D) GFP genotyping confirmed piPS cell contribution to multiple three germ layer tissues in chimeric fetuses, including heart, liver, brain, tail, and gonad tissues. A representative genomic PCR of GFP was shown for embryo 9 that also contains piPS cell germline contribution.

To examine the developmental potential of piPS cells, standard in vitro differentiation using embryoid bodies (EBs) or monolayer chemically defined step-wise differentiation, as well as in vivo chimerism assays were performed. piPS cells could efficiently form EBs in suspension, and differentiate into cells in the three primary germ layers, including endoderm derivatives: cells expressing AFP, Sox17, GATA4, or FoxA2, pancreatic cells (Pdx1), and hepatic cells (Albumin); mesoderm derivatives: cells expressing Brachyury, and mature beating cardiomyocytes (CT3 and MHC); and ectoderm derivatives: neural (Sox1, Pax6) and characteristic mature neuronal cells (βIII-tubulin, Map2ab) (FIGS. 2A, 2B, FIG. 4B). Most importantly, such piPS cells could efficiently incorporate into the inner cell mass of a blastocyst following aggregation with an 8-cell embryo, and led to high-level chimerism with apparent germline contribution in vivo after the aggregated embryos were transplanted into mice, as confirmed by GFP genotyping in multiple three germ layer tissues of E13.5 fetuses (FIG. 2D, FIG. 4C) and observation of Oct4-$GFP^+$ cells in the gonad tissue in 3 out of 17 fetuses (FIG. 2C). These in vitro and in vivo characterizations collectively confirm that the purified cell-penetrating recombinant reprogramming proteins are sufficient to reprogram MEFs to become piPS cells, which are molecularly, morphologically and functionally similar to conventional mES cells.

iPS cells (and especially patient-specific ones), which are similar to ES cells but are much easier to create and, in the case of human cells, less controversial, present unprecedented opportunities for biomedical research and clinical applications. Realization of the promise of iPS cells will require improved methods of directed differentiation for generating homogenous populations of lineage-specific cell types as well as elimination of the risks and drawbacks associated with the current iPS-cell protocol, including genetic manipulation, and the low efficiency/slow kinetics of induction. Recent advances in using various genetic approaches have addressed some of those iPS cell challenges, including using non-integrating adenoviruses to deliver reprogramming genes (Stadtfeld, M. et al., *Science*, 322, 945-949 (2008)), transient transfection of reprogramming plasmids (Okita, K. et al., *Science*, 322, 949-953 (2008)), a piggyBac transposition system (Woltjen, K. et al., *Nature*, 458, 766-770 (2009); Kaji, K. et al., *Nature*, 458, 771-775 (2009)), Cre-excisable viruses (Soldner, F. et al., *Cell*, 136, 964-977 (2009)), and oriP/EBNA1-based episomal expression system (Yu, J. et al., *Science*, DOI: 10.1126 (2009)). In addition, strategies of exploiting endogenous gene expression in certain cell types also allowed easier reprogramming and/or with less required exogenous genes (Shi, Y. et al., *Cell Stem Cell*, 2, 525-528 (2008b); Aasen, T. et al., *Nat Biotechnol*, 26, 1276-1284 (2008); Kim, J. B., Zaehres, H., et al., *Nature*, 454, 646-650 (2008)). Moreover, small molecules have been identified that enhance reprogramming efficiency and replace certain reprogramming factors (Shi, Y. et al., *Cell Stem Cell*, 2, 525-528 (2008b); Shi, Y. et al., *Cell Stem Cell*, 3, 568-574 (2008a); Li, W. et al., *Cell Stem Cell*, 4, 16-19 (2009); Huangfu, D. et al., *Nat Biotechnol*, 26, 795-797 (2008a); Huangfu, D. et al., *Nat. Biotechnol.*, 26, 1269-1275 (2008b)). However, all of those methods have yet to produce iPS cells without the use of any genetic material. Our present study is the first to demonstrate that somatic cells (i.e. murine fibroblasts) can be fully reprogrammed into pluripotent stem cells by direct delivery of recombinant reprogramming proteins. This protein transduction method represents a significant advance in generating iPS cells, and has several major advantages over previous iPS-cell methods. First, it effectively eliminates any risk of modifying target cell genome by exogenous genetic sequences, which are associated with all previous iPS-cell methods, and consequently offers a method for generating safer iPS cells. Second, the protein transduction method provides a substantially simpler and faster approach than the currently most advanced genetic method, which requires time-consuming sequential selection of potentially integration-free iPS cells. And finally, given the robustness and wide availability of large-scale recombinant protein production, our demonstrated completely chemically defined reprogramming regimen could potentially enable broader and more economical application of reprogramming methodology.

Plasmids Construction

Codons of human Pou5f1/Oct4 (NP_002692), Sox2 (NP_003097), Klf4 (NP_004226), and cMyc (NP_002458) were first optimized for high level protein expression in *E. coli*. They were then synthesized using DNA oligo based, PCR gene assembling method. Poly-arginine tag plus a linker sequence, i.e. ESGGGGSPGRRRRRRRRRRR (SEQ ID NO:2), was added to each protein C-terminal. The final DNA fragment was flanked with Nde I and Xho I sites, and inserted into pET41a expression vector Nde I-Xho I sites for protein expression. Each plasmid was verified by DNA sequencing.

Protein Expression and Purification

The above protein expression plasmids were individually transformed into BL21 (DE3) competent cells, and the recombinant protein production was carried out using auto-induction method. Briefly, proteins were expressed in cells by induction with 0.5 mM isopropyl-1-thio-β-D-galactopyranosid. The cells were then collected by centrifugation, and the pellets were subjected to freeze-and-thaw cycles. The inclusion bodies released were first washed extensively with a buffer containing 8 M urea, 100 mM Tris, 1 mM glycine and 10 mM B-Mercaptoethanol (pH8). The solubilized inclusion bodies were refolded with a rapid dilution method as described previously (Hou, W. et al., *Clin Cancer Res*, 11, 5595-5602 (2005); Lafevre-Bernt, M., Wu, S., and Lin, X., *Mol Cancer Ther*, 7, 1420-1429 (2008); Medynski, D. et al., *Protein Expr Purif,* 52, 395-402 (2007)). The refolded protein was concentrated using tangential flow filtration and purified by size exclusion chromatography using a Superdex-200 column (XK26×850-mm, GE, Piscataway, N.J.), and confirmed using SDS-PAGE.

Western Blotting

We used Nanodrop ND-1000 to measure purified protein concentration (A280). Protein samples were separated on Novex® 4-20% Tris-Glycine Gel and blotted onto nitrocellulose membrane (GE, USA). For identification of recombinant proteins, Oct3/4 (sc-5279; Santa Cruz Biotechnology, USA), Sox2 (AP2048d; Abgent, USA), Klf4 (AF3640-pu, R&D, USA) and cMyc (AF3696, R&D, USA) antibodies were used. Anti-mouse, anti-rabbit and anti-goat HRP-conjugated IgGs (Cell Signalling Technology) were used as secondary antibodies. Signals were detected using SuperSignal West Femto Chemiluminescent Substrate (Thermo Scientific, USA).

Cell Culture

OG2-MEFs were cultured on gelatin-coated dishes in normal MEF media: high-glucose D-MEM (Invitrogen) with 10% FBS, 0.1 mM non-essential amino acids, and 2 mM L-glutamine. piPS cells were cultured on irradiated CF1 MEFs with normal mESC growth media, which consist of Knockout DMEM (Invitrogen) supplemented with 20% KSR, 0.1 mM 2-ME, 2 mM L-glutamine, 0.1 mM non-essential amino acids, and $10^3$ units/ml LIF (ESGRO, Chemicon International). The piPS cells were passaged every 3 days as a single cell suspension using 0.05% trypsin/EDTA and seeded at $1.0 \times 10^4$ cells per cm$^2$ for routine culture. For feeder-free culture, cells are grown on gelatin-coated tissue culture dishes in chemically defined media, which consist of Knockout DMEM supplemented with 1×N$^2$, 1×B27, 0.1 mM 2-ME, 2 mM L-glutamine, 0.1 mM non-essential amino acids, 50 μg/ml BSA fraction V (GIBCO), $10^3$ units/ml LIF and 10 ng/ml BMP4 (R&D).

Generation of piPS Cells

OG2-MEFs were seeded at $5 \times 10^4$ cells per well in a 6-well plate coated with gelatin in normal MEF media (DMEM supplemented with 10% FBS). On the next day, media was changed to the protein transduction media, which were prepared by mixing the recombinant reprogramming proteins at the final concentration of 8 μg/ml with regular mES cell growth medium supplemented with $10^3$ units/ml LIF. After overnight culture in the protein transduction media, media was changed to normal mESC growth media, and cells were cultured for additional 36 hours before repeating the same protein transduction cycle. Total four protein transduction cycles were applied on the cells. After completing protein transduction, cells were then passaged onto irradiated CF-1 MEF feeder cells at day 9 in normal mESC growth media. Media were changed every 3-4 days until GFP$^+$ colonies were observed around day 30-35. GFP$^+$ colonies were then passaged onto new irradiated MEF feeder cells in normal mESC growth media, and stably maintained and expanded as piPS cells. Some colonies were further selected and expanded in the presence of pluripotin (1 μM) or PD0325901 (1 μM).

Spontaneous In Vitro Differentiation

The pluripotency of piPSCs were examined by in vitro differentiation from embryoid bodies (Ebs). piPSCs were trypsinized into single cells and cultured in suspension on low adhesion plates (Corning) in DMEM medium supplemented with 10% FBS. Media were refreshed every other day and Ebs were allowed to grow for 6 days in suspension. Ebs were then replated onto 0.1% gelatin-coated plates. Spontaneous differentiations were examined by immunostaining or RT-PCR of representative lineage specific markers with indicated antibodies or primers at various time points (3 up to 16 days).

Cytochemistry and Immunofluorescence Assay:

ALP staining was performed using the Alkaline Phosphatase Detection Kit (Chemicon) as instructed by the manufacturer. Immunocytochemistry was performed using standard protocol. Briefly, cells were fixed in 4% paraformaldehyde (Sigma-Aldrich), washed three times by PBS, and then incubated in PBS containing 0.3% TritonX-100 (Sigma-Aldrich) and 5% normal donkey serum (Jackson Immuno Research) for 1 hr at room temperature. The cells were then incubated with primary antibody at 4° C. overnight: Albumin (Abcam, AB19188, 1:200); Brachyury (Santa Cruz, C-19, 1:200); Cardiac troponin t antibody (CT3) (Developmental Studies Hybridoma Bank, 1:700); Gata4 (Santa Cruz, H-112, 1:300); MAP2ab (Abcam, ab5392, 1:1000); MF20 (Developmental Studies Hybridoma Bank, 1:200); Nanog (Abcam, ab21603, 1:500); Oct4 (Santa Cruz, sc-5279, 1:100); Pax6 (Developmental Studies Hybridoma Bank, 1:2000); Pdx1 (Millipore, AB3243, 1:500); Sox2 (Millipore, AB5603, 1:500); Sox17 (R&D systems, AF1924, 1:300); SSEA1 (Santa Cruz, sc-21702, 1:100); Tuj-1 (Covance, MMS-435P, 1:1000). After washing three times with PBS, cells were incubated with secondary antibodies: Alexa Fluor 555 donkey anti-mouse IgG (1:2000, Invitrogen), Alexa Fluor 555 donkey anti-goat IgG (1:2000, Invitrogen), Alexa Fluor 555 donkey anti-chicken IgG (1:2000, Invitrogen), or Alexa Fluoro 555 donkey anti-rabbit IgG (1:2000, Invitrogen) for 2 hr at RT. Nuclei were detected by DAPI (Sigma) staining Images were captured by Zeiss HXP 120.

Semi-Quantitative RT-PCR

Total RNAs were extracted using Rneasy plus mini kit (Qiagen), reverse transcribed with iScript cDNA Synthesis Kit (BioRad) according to manufacturers' instructions. PCR products were resolved on (1.5%) agarose gels and visualized by ethidium bromide staining Images were taken using Bio-Rad Gel document system. Primers used are listed in Table 1.

Bisulfite Sequencing Analysis

DNAs from R1 cells, OG2 MEFs, and piPS cells (passage 9) were isolated using the Non Organic DNA Isolation Kit (Millipore). The DNAs were then treated for bisulfite sequencing with the EZ DNA Methylation-Gold Kit (Zymo Research Corp., Orange, Calif.). The treated DNAs were then used to amplify sequences of interest. Primers used for promoter fragment amplification were as previously published (Blelloch et al., 2006) and listed in Table 1. The resulting fragments were cloned using the TOPO TA Cloning Kit for sequencing (Invitrogen) and sequenced.

Microarray Analysis

The Illumina Sentrix BeadChip Array MouseRef-8 v2 (Illumina, CA, USA) was used for microarray hybridizations to examine the global gene expression of murine ES cells, piPS cells and OG2-MEFs. Biotin-16-UTP-labeled cRNA was synthesized from 500 ng total RNA with the Illumina Total-Prep RNA amplification kit (Ambion AMIL1791, Foster City, Calif., USA). The hybridization mix containing 750 ng of labeled amplified cRNA was prepared according to the Illumina BeadStation 500X System Manual (Illumina, San Diego, Calif., USA) using the supplied reagents and GE Healthcare Streptavidin-Cy3 staining solution. Hybridization to the Illumina Array MouseRef-8 v2 was for 18 h at 55° C. on a BeadChip Hyb Wheel. The array was scanned using the Illumina BeadArray Reader. All samples were prepared in two biological replicates. Processing and analysis of the microarray data were performed with the Illumina BeadStudio software. The data were subtracted for background and normalized using the rank invariant option.

Chimera Formation piPS cells were aggregated with denuded post-compacted eight-cell stage embryos to obtain aggregate chimeras. Eight-cell embryos were flushed from females at 2.5 dpc and cultured in microdrops of KSOM medium (10% FCS) under mineral oil. Clumps of piPS cells (10-20 cells) after short treatment of trypsin were chosen and transferred into microdrops containing zona-free eight-cell embryos. Eight-cell embryos aggregated with piPS cells were cultured overnight at 37° C., 5% $CO_2$. Aggregated blastocysts that developed from eight-cell stage were transferred into one uterine horn of a 2.5 dpc pseudopregnant recipient.

TABLE 1

| Gene | Forward (SEQ ID NO:) | Reverse (SEQ ID NO:) |
|---|---|---|
| For RT-PCR | | |
| AFP | ACAGGAGGCTATGCATCACCAGTT (11) | TGCTCCTCTGTCAGTTCAGGCTTT (12) |
| Brachyury | ATGCCAAAGAAAGAAACGAC (13) | AGAGGCTGTAGAACATGATT (14) |
| cMyc | CAGAGGAGGAACGAGCTGAAGCGC (15) | TTATGCACCAGAGTTTCGAAGCTGTTCG (16) |
| E-cad | GCAGTCAGATCTCCCTGAGTTCGAG (17) | CTACATACAAAGGTCACTCTAGCAAC (18) |
| FoxA2 | AAGGGAAATGAGAGGCTGAGTGGA (19) | ATGACAGATCACTGTGGCCCATCT (20) |
| GAPDH | GTGTTCCTACCCCCAATGTGT (21) | ATTGTCATACCAGGAAATGAGCTT (22) |
| Klf4 | CACCATGGACCCGGGCGTGGCTGCCAGAAA (23) | TTAGGCTGTTCTTTTCCGGGGCCACGA (24) |
| Nanog | AGGGTCTGCTACTGAGATGCT (25) | CAACACCTGGTTTTTCTGCCACCG (26) |
| Oct4 | CTGAGGGCCAGGCAGGAGCACGAG (27) | CTGTAGGGAGGGCTTCGGGCACTT (28) |
| Otx2 | CCGACTTTGCGCCTCCAAACAA (29) | GGTTGATGGACCCTTCTAAGGC (30) |
| Pax6 | GCTTCATCCGAGTCTTCCCGTTAG (31) | CCATCTTGCTTGGGAAATCCG (32) |
| Pdx1 | CTCCGCCGCCACCCCAGTTTAC (33) | GCGGGGCCGGGAGATGTATTTG (34) |
| Rex-1 | TGAAAGTGAGATTAGCCCCGAG (35) | GTCCCATCCCCTTCAATAGCAC (36) |
| Sox1 | CCTCGGATCTCTGGTCAAGT (37) | TACAGAGCCGGCAGTCATAC (38) |
| Sox2 | GGTTACCTCTTCCTCCCACTCCAG (39) | TCACATGTGCGACAGGGGCAG (40) |
| Sox17 | TGCCCTTTGTGTATAAGCCCGAGA (41) | GGGTAGTTGCAATAGTAGACCGCT (42) |
| For bisulfite-sequencing PCR | | |
| Oct4 | GTTGTTTTGTTTTGGTTTTGGATAT (43) | CCACCCTCTAACCTTAACCTCTAAC (44) |
| Oct4 | ATGGGTTGAAATATTGGGTTTATTTA (45) | CCACCCTCTAACCTTAACCTCTAAC (44) |
| Nanog | GAGGATGTTTTTTAAGTTTTTTTT (46) | CCCACACTCATATCAATATAATAAC (47) |
| Nanog | AATGTTTATGGTGGATTTTGTAGGT (48) | CCCACACTCATATCAATATAATAAC (47) |

Example 3

A-83-01, PD0320501, and CHIR99021 Treatment Enhanced iPSC Generation

We tested the TGFβ receptor inhibitor (A-83-01), MEK inhibitor (PD0325901) and GSK-3 inhibitor (CHIR99021), on mouse fibroblast cells that were treated with exogenous Oct4, Klf4, Sox2 and c-Myc polypeptides, for their effects on reprogramming kinetics and efficiency.

Figure 5:
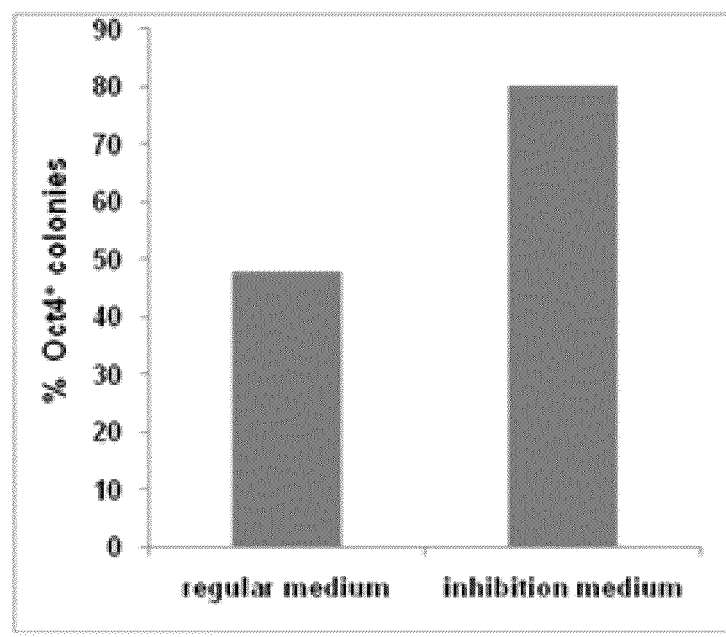
FIG. 5. A-83-01, PD0320501, and CHIR99021 treatment enhanced iPSC generation. A comparison of the number of Oct4$^+$ iPS cell colonies generated from mouse fibroblast cells treated with exogenous Oct4/Sox2/Klf4/Myc polypeptides, and with or without 0.5 μM PD0325901, 3 μM CHIR99021, and 0.5 μM A-83-01. Y-axis represents percentage of Oct4' colonies within total number of colonies.

Mouse fibroblasts were grown in mESC growth medium [Knockout DMEM (Invitrogen) supplemented with 10% ES-FBS+10% KSR, 0.1 mM 2-ME, 1% Glutamax, 1% Non-essential amino acids, 1% EmbryoMax ESC Qualified Nucleosides (Millipore), and $10^3$ units/ml LIF (ESGRO, Chemicon International)] supplemented with 8 µg/ml of Oct4/Sox2/Klf4/Myc (all four transcription factors are tagged with poly-Arg ESGGGGSPGRRRRRRRRRRR; SEQ ID NO:2) for 4-12 hours, followed by culturing the cells in the absence of the Oct4/Sox2/Klf4/Myc polypeptides for one day. This procedure was repeated 4 times. The cells were then cultured in mESC medium for another two weeks. iPSC clones were detected by colony morphology and expression of pluripotency markers. An intermediate iPSC clone, which expresses ALP but not Oct4 (Oct4), was dissociated with Trypsin-EDTA. The clone was then expanded by continuous culturing with regular mESC medium or medium supplemented with 0.5 µM PD0325901, 3 µM CHIR99021, 0.5 µM A-83-01. The number of Oct4-positive colonies were counted 2 weeks after small molecule treatment (FIG. 5). The treatment of PD0325901, CHIR99021, and A-83-01 increases reprogramming efficiency and accelerates reprogramming kinetics by promoting intermediate piPS cells to stable and fully reprogrammed piPS cells.

The above examples are provided to illustrate the invention but not to limit its scope. Other variants of the invention will be readily apparent to one of ordinary skill in the art and are encompassed by the appended claims. All publications, databases, Genbank sequences, patents, and patent applications cited herein are hereby incorporated by reference.

What is claimed is:

1. A method of producing an induced pluripotent stem cell from a mammalian non-pluripotent cell, the method comprising:
    contacting the non-pluripotent cell with a plurality of exogenous transcription factor polypeptides, each exogenous transcription factor polypeptide comprising a transcription factor fused to a heterologous peptide sequence that enhances transport across cell membranes, under conditions to produce the induced pluripotent stem cell from the mammalian non-pluripotent cell;
    wherein the exogenous transcription factor polypeptides are selected from the group consisting of: (i) Oct4, Klf4, and Sox2; and (ii) Oct4, Klf4, Sox2, and c-Myc; and
    contacting the non-pluripotent cell with a MEK inhibitor, a GSK3 inhibitor, and a TGFβ receptor inhibitor/ALK5 inhibitor.

2. The method of claim 1, wherein the heterologous peptide is selected from the group consisting of *Drosophila* homeoprotein antennapedia transcription protein (AntHD), herpes simplex virus structural protein VP22, the HIV-1 transcriptional activator TAT protein, Kaposi FGF signal sequence (kFGF), protein transduction domain-4 (PTD4), Penetratin, M918, Transportan-10, a nuclear localization sequence, a PEP-I peptide; an amphipathic peptide; a delivery enhancing transporter, and a peptide sequence comprising at least 5 or more contiguous arginines.

3. The method of claim 1, wherein the heterologous peptide is a peptide sequence comprising RRRRRRRRRRR (SEQ ID NO:1).

4. The method of claim 1, wherein the non-pluripotent cell is contacted with an exogenous Klf4 polypeptide, an exogenous Oct4 polypeptide, and an exogenous Sox2 polypeptide.

5. The method of claim 1, wherein the non-pluripotent cell is contacted with an exogenous Klf4 polypeptide, an exogenous Oct4 polypeptide, an exogenous c-Myc polypeptide, and an exogenous Sox2 polypeptide.

6. The method of claim 1, wherein the non-pluripotent cell is not contacted with a Nanog polypeptide.

7. The method of claim 1, wherein the non-pluripotent cell is not contacted with a protein delivery agent.

8. The method of claim 1, wherein the contacting step comprises at least two cycles of:

(i) contacting the non-pluripotent cell with the exogenous polypeptides followed by culturing the cell in the absence of the exogenous polypeptides.

9. The method of claim 8, further comprising purifying the pluripotent cell to generate a homogenous population of pluripotent cells.

10. The method of claim 1, wherein the cell is a mouse cell.

11. The method of claim 1, wherein the cell is a human cell.

12. The method of claim 1, wherein the cell is a non-human cell.

13. The method of claim 1, further comprising contacting the cell with one or more of:
   a histone deacetylase (HDAC) inhibitor; and
   a DNA methyltransferase (DNMT) inhibitor.

14. The method of claim 1, further comprising contacting the cell with one or more of:
   an agent that inhibits H3K9 methylation;
   an L-type Ca channel agonist;
   an activator of the cAMP pathway;
   a nuclear receptor ligand;
   an erk inhibitor
   a histone deacetylase (HDAC) inhibitor; and
   a DNA methyltransferase (DNMT) inhibitor.

* * * * *